United States Patent [19]

Jeffreys

[11] Patent Number: 5,175,082

[45] Date of Patent: Dec. 29, 1992

[54] METHOD OF CHARACTERIZING GENOMIC DNA

[75] Inventor: Alec J. Jeffreys, Leicester, United Kingdom

[73] Assignee: Imperial Chemical Industries PLC, London, England

[21] Appl. No.: 27,858

[22] Filed: Mar. 19, 1987

[30] Foreign Application Priority Data

Mar. 19, 1986 [GB] United Kingdom ................. 8606719

[51] Int. Cl.⁵ ........................ C12Q 1/68; C07H 21/04
[52] U.S. Cl. ........................................ 435/6; 536/27; 536/28; 536/29; 514/44; 935/78
[58] Field of Search .................. 435/6; 536/27, 28, 29

[56] References Cited
FOREIGN PATENT DOCUMENTS

| | | |
|---|---|---|
| 0084796 | 3/1983 | European Pat. Off. |
| 0164054 | 12/1985 | European Pat. Off. |
| 8303260 | 3/1983 | PCT Int'l Appl. |
| 8607464 | 12/1986 | PCT Int'l Appl. |
| 2135774 | 5/1984 | United Kingdom |
| 2166445 | 5/1986 | United Kingdom |
| 8602948 | 5/1986 | World Int. Prop. O. |
| 8606102 | 10/1986 | World Int. Prop. O. |
| 8907658 | 8/1989 | World Int. Prop. O. |

OTHER PUBLICATIONS

Nicholls et al, "Direct Cloning of Specific Genomic DNA Sequences in Plasmid Libraries Following Fragment Enrichment", Nucleic Acids Research, 1985, 13, (21), 7569-7578.
Litt et al, "A Highly Polymorphic Locus in Human DNA revealed by Cosmid-Derived Probes", Proc. Natl. Acad. Sci. USA, vol. 82, pp. 6206-6210, Sep. 1985, Genetics.
Nakamura et al, "Variable Number of Tandem Repeat (VNTR) Markers for Human Gene Mapping", Science, 1987, 235, 1616-1622.
Hache et al, "A Rapidly Growing RecBC⁻ Strain of *E. coli* Applications for Problem Cloning." *Nucleic Acids Research*, 1989, 17, (9), 3609.
Wyman et al, "Host Strains That Alleviate Underrepresentation of Specific Sequences: Overview", Methods in Enzymology, 1987, 152, 173-180.
Wong et al., (1987) *Ann. Hum. Genetics* 51:269-88.
Jeffreys et al., Abstract of Talk to Poultry Research Center, circulated Oct. 22, 1984.
Bell et al., (1981) *Proc. Natl. Acad. Sci.* 78(9):5759-63.
Goodbourne et al., (1984) *Mol. Biol. Med* 2:223-8.
Higgs et al., (1986) *Proc. Natl Acad. Sci.* 83:5165-9.
Jarman et al., (1986) EMBO Journal 5(8):1857-63.
Caskey, (1985) *Nature* 314:19.
Jeffreys et al., (1985) Nature 314(6006):67-73.
Jeffreys et al., (1985) Nature 316:76-79.
Wong et al., (1986) Nucleic Acids Research 14(11):4605-4616.
Bell et al., (1982) Nature 295:31-35.
Capon et al., (1983) Nature 302:33-37.
Stoker et al., (1985) Nucleic Acids Research 13(13):4613-4622.
Goodbourn et al., (1983) Proc. Natl. Acad. Sci. USA 80:5022-5026.
Wyman et al, (1980) Proc. Natl. Acad. Sci. USA 77(11):6754-6758.

(List continued on next page.)

*Primary Examiner*—Johnnie R. Brown
*Assistant Examiner*—L. Eric Crane
*Attorney, Agent, or Firm*—Cushman, Darby & Cushman

[57] ABSTRACT

Test samples of genomic DNA may be characterized by the use of polynucleotide probes each of which is specific for an informative genetic locus. Such probes may be prepared by the use of probes which are capable of differentiating DNA by reference to more than one polymorphic minisatellite region or hypervariable locus. The polynucleotides and probes of the invention are of use for genetic identification purposes, paternity and maternity testing and particularly in forensic medicine.

8 Claims, 13 Drawing Sheets

OTHER PUBLICATIONS

Balazs et al., (1982) Proc. Natl. Acad. Sci. USA 79:7395-7399.
Sykes et al., (1985) Hum. Genet. 70:35-37.
Wyman et al., (1985) Proc. Natl. Acad. Sci. USA 82:2880-2884.
Baird et al., (1986) Am. J. Hum. Genet. 39:489-501.
White et al., (1985) Nature 313:101-105.
Weller et al., (1984) EMBO Journal 3:(2):439-446.
Gill et al., (1985) Nature 318:577-579
Yang et al., (1982) Proc. Natl. Acad. Sci. USA 79:6593-6597.
Proudfoot et al., (1982) Cell 31:553-563.
Beauchamp et al. (1979) Chromosoma (Berl.) 71, 153-166.
Anderson et al. (1981) Nature, 290, 457-465.
Maxam et al. (1977) Proc Natl Acad Sci, 74(2), 560-564.
Sanger et al. (1977) Proc Natl Acad Sci, 74(12) 5463-5467.
Principles of Gene Manipulation, Third Edition, R. W. Old and S. B. Primrose, authors, Blackwell Scientific Publications, 1985, pp. 8-10. 120-121.
Jeffreys et al., (1985) *Nature* 317:818-819.
Jeffreys et al., (1986) American Journal of Human Genetics 39:11-24.
Crawford et al., (1986) Journal of Medical Genetics 23(5):471.
Yang et al., (1984) Chemical Abstracts 100:118, abstract No. 80593s.

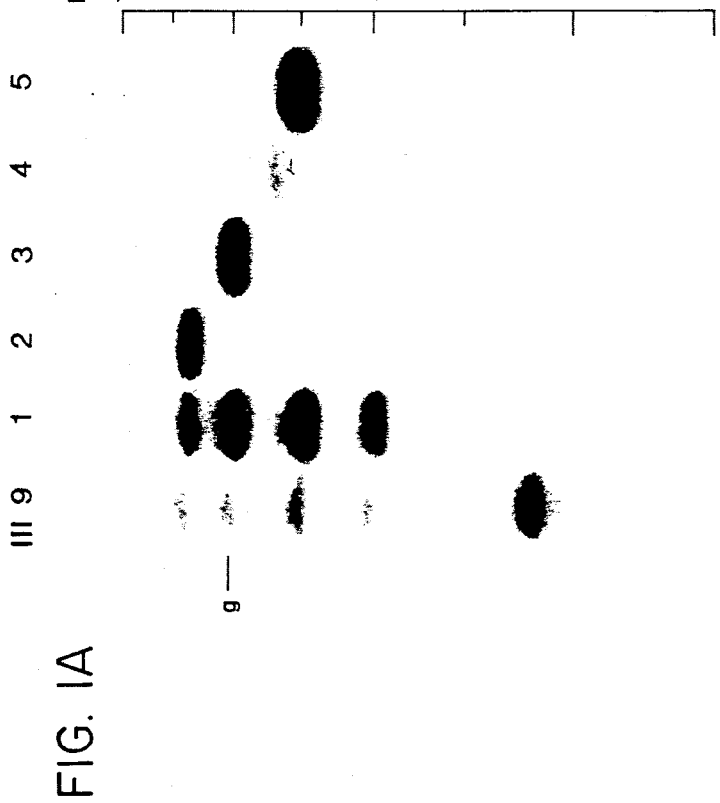
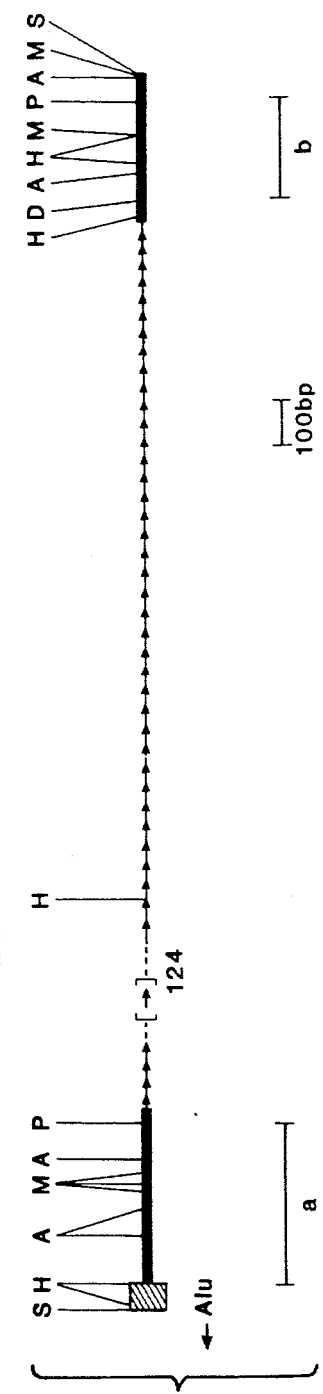
FIG. IA
FIG. IB

GATCCACCCGCCTCGGCCTCCCAAAGTGCTGGGATTACAGGCGTGACCACCGCCCGGCcgcattcatggttttatttgttcctgttcctctaaca tagatggaagtcacacaaagcaaggacttgctcatgatttatctctgcctcaaggtagctgtggtgcaaggagatgtgcagtaaatatttgcgg caggaagaaggaaagaatgcagctagcaaggaggaagat tgggaggaaggaaacaagaggaaggaaagaggaggggg gcggggagtatttcacctcctgaagctctctgtccctgaaggggaggggctgctcataccaccaccaccccaccacaggcagagtaag aggctgcctgcagattgcctgagtaggacgtgcggtg

| | | | | | | |
|---|---|---|---|---|---|---|
| GC | T | C | | C | G | 1 |
| GC | T | A | | | A | 2 |
| | T A | CA | | | A | 3 |
| GC | T | | | | A | 4 |
| | T | C | | | G T | 5 | con    AGGAATAGAAAGGCGGGYGGTGTGGGCAGGGAGRGGC

| | | | | |
|---|---|---|---|---|
| T | G | | | α |
| C | A | | C | |
| C | A | | C | |
| C | G | | | |
| T | G | | | |

```
         cagtgacaggcctgcttcccgcataggagcagcatgaggtgctgagaggaacaga
cattgctgtaagcagggtgggatgcacacaataatattcccagcttctcgtgttgtgtgggcccattctgctgcaaaccagtaggataattccaccag
cacgttgggttggaagaacagaaggaggcagagtggctgggtgcgaccatcatggagagttcacaggacacgagggaggagaggagtgctgggtcgcg
gtgctgcagatacgcagcgtctcacagaccaggaaagagagctttgcagatc
```

```
con    AGGAATAGAAAGGCGGGYGGTGTGGGCAGGGAGRGGC
        *      *********  **
core           GGAGGTGGGCAGGARG
```

Fig.6.

```
core                                    GGAGGTGGGCAGGARG                              length, bp
                                        ────────────────                                   16 detected by 33.15:

pλg3         agaaaggcgggyGgtGTGGGCAGGgAGrggcaggaat                                         37
                             ||||||||||||||||
λMS1                         GTGGaYAGG                                                      9
                             |||||||||
λMS31                      tgGGGAGGTGGGRYAGtgtctg                                           20
                           |||||||||||||||||
λMS32             gaatggaGcAGGYGRcCAGGGtgactca                                              29
                         |||||||||||||||| derived core                            GGAGGTGGNCAGGRRG detected by 33.6:

λMS8  1:                   gggctggGGGAGaTGGtggaGgAGgtgttgg                                  30
      2:                   aggctgGGGAGaTGGtggaGgAagagt-ac                                   29
λMS43      tgtgtgtaatgggtatagGGaGGGCcccgGGaaggggggtgtggy                                    45
```

METHOD OF CHARACTERIZING GENOMIC DNA

The present invention relates generally to polynucleotides and DNA and RNA probes, their preparation and their use in genetic characterization. Such uses may include for example establishing human, animal or plant origin, and the polynucleotides and probes of the invention may thus find use for example in paternity disputes or forensic medicine or in the prevention, diagnosis and treatment of genetic disorders or predispositions.

In British patent application no. 8525252 (publication no. 2166445) there are described various DNA sequences which may be used as probes to hybridize individually at a number of polymorphic sites within the human and animal genomes enabling the production of a "fingerprint" composed of marked bands of differing molecular weights. The fingerprint as a whole is characteristic of the individual concerned and the origin of the differing bands can be traced through the ancestry of the individual and can in certain cases be postulated as associated with certain genetic disorders.

The present invention is based upon the discovery that informative genetic loci may be identified in the genome by the use of multi-locus probes and that polynucleotides and polynucleotide probes may be prepared each of which is specific for a single such informative genetic locus.

Hitherto, only a limited number of hypervariable loci have been discovered in human DNA; these include minisatellites 5' to the insulin gene (Bell, Selby and Rutter, 1982), 3' to the c-Ha-ras1 gene (Capon et al., 1983), type II collagen gene (Stoker et al., 1985) and between the ζ2 and ψζ1 globin genes (Goodbourn et al., 1983) as well as the D14S1 locus defined by an anonymous DNA clone derived from the telomeric region of the long arm of chromosome 14 (Wyman and White, 1980; Balazs et al., 1982; Wyman, Wolfe and Botstein, 1984). These minisatellites differ substantially in their variability, ranging from only 6 different alleles detected at the collagen hypervariable region (Sykes, Ogilvie and Wordsworth, 1985) to more than 80 at the D14S1 locus (Balazs et al., 1986). The total number of hypervariable loci in the human genome is unknown but is likely to be large. Indeed the human genome might contain at least 1500 hypervariable regions.

It has been found that it is possible to clone a DNA fragment identified by hybridization of fragments of genomic DNA with a polynucleotide probe capable of differentiating DNA by reference to more than one polymorphic minisatellite region or hypervariable locus, for example the probes 33.6 and 33.15 described and claimed in the aforementioned British Patent Application No. 8525252 (publication No. 2,166,445), and to prepare therefrom a polynucleotide or probe capable of hybridizing to a DNA fragment which contains a minisatellite which is specific as to a particular region or locus on the genome, said region or locus being an informative genetic locus. In this specification we define an informative genetic locus as one at which at least 3 different alleles can be distinguished in any sample of 100 randomly selected unrelated individuals. This is expressed herein by stating that the locus has an allelic variation of at least 3(100). Preferably the sample of randomly selected unrelated individuals will be 500, more preferably 1000, and the ability to distinguish at least 3 different alleles in such samples is referred to herein as 3 (500) and 3(1000) respectively. It is essential that the sample of 100, 500 or 1000 randomly selected unrelated individuals is indeed selected at random as it will usually be possible to identify 100, 500 or 1000 individuals who have less than 3 alleles at a given informative genetic locus by screening a sufficiently large number of members of the total population.

The higher is this polymorphism at a given informative genetic locus, the more useful and informative will be the locus specific probe in genetic characterization for example in individual identification for paternity or forensic evaluation.

It will be appreciated in this regard that the term "individual" has been used above to refer not only to humans, but also to other animals as well as to plants and to cell lines derived from such humans, animals and plants. In each case, however, the sample of randomly selected unrelated individuals will all be from the same species.

In respect of the human applications of the present invention the expression "informative genetic locus" as used herein may alternatively be defined as one at which at least 3 different alleles can be distinguished in DNA extracted from any 20 cell lines selected from the following, which cell lines have been deposited with the American Type Culture Collection (ATCC):

| Cell Line | ATCC Deposit No. |
| --- | --- |
| Hela | CCL2 |
| RPMI 2650 | CCL 30 |
| Detroit 532 | CCL 54 |
| Detroit 525 | CCL 65 |
| Detroit 529 | CCL 66 |
| Detroit 510 | CCL 72 |
| WI-38 | CCL 75 |
| Citrullinemia | CCL 76 |
| EB-3 | CCL 85 |
| RAJI | CCL 86 |
| JIYOYE (P-2003) | CCL 87 |
| WI-26 | CCL 95 |
| Detroit 551 | CCL 110 |
| RPMI 6666 | CCL 113 |
| RPMI 7666 | CCL 114 |
| CCRF-CEM | CCL 119 |
| CCRF-SB | CCL 120 |
| HT-1080 | CCL 121 |
| HG 261 | CCL 122 |
| CHP3 (M.W.) | CCL 132 |
| LL47 (MaDo) | CCL 135 |
| HEL 299 | CCL 137 |
| LL 24 | CCL 151 |
| HFLI | CCL 153 |
| WI-1003 | CCL 154 |
| MRC-5 | CCL 171 |
| IMR-90 | CCL 186 |
| LS 174T | CCL 188 |
| LL 86(LeSa) | CCL 190 |
| LL 97A (AIMy) | CCL 191 |
| HLF-a | CCL 199 |
| CCD-13Lu | CCL 200 |
| CCD-8Lu | CCL 201 |
| CCD-11Lu | CCL 202 |
| CCD-14Br | CCL 203 |
| CCD-16Lu | CCL 204 |
| CCD-18Lu | CCL 205 |
| CCD-19Lu | CCL 210 |
| Hs888Lu | CCL 21 |
| MRC-9 | CCL 212 |
| Daudi | CCL 213 |
| CCD-25Lu | CCL 215 |
| SW403 | CCL 230 |
| NAMALWA | CRL 1432 |

All the above-mentioned cell lines are freely available from the ATCC, 12301 Parklawn Drive, Rockville, Md. 20852-1776, USA and are listed in the ATCC catalogue of Cell Lines and Hybridomas. All the abovementioned cell lines were on deposit with the ATCC prior to 1985.

Thus according to one feature of the present invention there is provided a method of preparing a polynucleotide capable of hybridizing to a DNA fragment which contains a minisatellite which is specific as to a particular region or locus in the genome, said region or locus having an allelic variation (as is hereinbefore defined) of at least 3(100), which method comprises cloning a DNA fragment identified by hybridization of fragments of genomic DNA with a polynucleotide probe which is capable of differentiating DNA by reference to more than one polymorphic minisatellite region or hypervariable locus;

and preparing therefrom a polynucleotide capable of hybridizing to a DNA fragment which contains a minisatellite which is specific as to a particular region or locus in the genome, said region or locus having an allelic variation (as hereinbefore defined) of at least 3(100).

According to a further feature of the present invention there is provided a method of preparing a polynucleotide capable of hybridizing to a DNA fragment which contains a minisatellite which is specific as to a particular region or locus in the genome, said region or locus having a degree of polymorphism of at least 3 (as hereinbefore defined), which method comprises cloning a DNA fragment identified by hybridisation of fragments of genomic DNA with a polynucleotide probe which is capable of differentiating DNA by reference to more than one polymorphic minisatellite region or hypervariable locus;

and preparing therefrom a polynucleotide capable of hybridizing to a DNA fragment which contains a minisatellite which is specific as to a particular region or locus in the genome, said region or locus having a degree of polymorphism of at least 3 (as hereinbefore defined).

Preferably the polynucleotide probe comprises, with the inclusion of a labeled or marker component, a polynucleotide comprising at least three tandem repeats (there being on average at least 70% homology between all tandemly repeated sequences) of sequences which are homologous with a minisatellite region of the genome to a degree enabling hybridisation of the probe to a corresponding DNA fragment obtained by fragmenting the sample DNA with a restriction endonuclease, wherein:

a) the repeats each contain a core which is at least 70% homologous with a consensus core region of similar length present in a plurality of minisatellites from different genomic loci;

b) the core is from 6 to 16 nucleotides long;

c) the total number of nucleotides within the repeating unit which do not contribute to the core is not more than 15.

Advantageously the said DNA fragment contains a minisatellite from a minisatellite region or hypervariable locus which region or locus is detectable by a polynucleotide probe comprising at least three tandem repeats of the sequence (including complementary sequences):

(A)AGGGCTGGAGG  1

(wherein T is T or U and (A) may be present or absent) or the sequence (including complementary sequences):

AGAGGTGGGCAGGTGG  2

(wherein T is T or U).

According to a further feature of the present invention there is provided a polynucleotide in isolated or cloned form, which comprises a nucleotide sequence which is specific as to a single minisatellite region or hypervariable locus and which is homologous therewith to a degree enabling hybridization of the nucleotide sequence to a corresponding DNA fragment obtained by fragmenting sample genomic DNA with a restriction endonuclease, the said DNA fragment containing a minisatellite from said minisatellite region or hypervariable locus, wherein:

1) said region or locus has an allelic variation (as herein defined) of at least 3(100) and 2) said region or locus is detectable by a polynucleotide probe comprising at least three tandem repeats of the sequence (including complementary sequences):

(A)AGGGCTGGAGG  1

(wherein T is T or U and (A) may be present or absent or the sequence (including complementary sequences):

AGAGGTGGGCAGGTGG  2

(wherein T is T or U).

The present invention also relates to a corresponding polynucleotide in which the aforesaid region or locus has a degree of polymorphism of at least 3 as opposed to an allelic variation of at least 3.

According to further features of the present invention the polynucleotides of the present invention and polynucleotides prepared by the hereinbefore defined method of the invention are prepared by microbiological reproduction of cloned material or by direct synthesis.

The invention includes polynucleotides of DNA, RNA and of any other kind hybridisable to DNA. The polynucleotides as defined above are unlabelled and can be in double stranded (ds) or single stranded (ss) form.

The invention includes labelled polynucleotides in ss-form for use as probes as well as their labelled ds-precursors, from which ss-probes can be produced.

Thus according to a further feature of the present invention there is provided a polynucleotide probe which comprises a polynucleotide of the present invention as hereinbefore defined or a polynucleotide prepared by a method as hereinbefore defined having a labelled or marker component. Generally at least the nucleotide sequence of the polynucleotide will be in single stranded form, but preferably the probe will comprise the polynucleotide wholly in single stranded form.

According to a further feature of the present invention there is provided a method of preparing a polynucleotide probe as hereinbefore defined which comprises labelling or marking a polynucleotide of the present invention as hereinbefore defined or a polynucleotide prepared by a method of the present invention as hereinbefore defined.

The polynucleotide probes of the present invention are preferably $^{32}P$-radiolabelled in any conventional way, but can alternatively be radiolabelled by other means well known in the hybridisation art for example to give $^{35}$S-radiolabelled probes. They may also be labelled with biotin or a similar species by the method of D C Ward et al, as described in Proceedings of the 1981 ICN-UCLA Symposium on Developmental Biology using Purified Genes held in Keystone, Colo. on Mar. 15-20, 1981 vol. XXIII 1981 pages 647-658 Academic Press; Editor Donald D Brown et al or even enzyme-labelled by the method of A D B Malcolm et al, Abstracts of the 604th Biochemical Society Meeting, Cambridge, England (meeting of Jul. 1, 1983).

According to a further feature of the present invention there is provided a method of characterizing a test sample of genomic DNA by reference to one or more controls which comprises fragmenting sample DNA with one or more restriction enzymes which do not cleave to any relevant extent a sequence corresponding to a tandem repeat, probing the DNA fragments with a polynucleotide or polynucleotide probe comprising a nucleotide sequence which is specific as to a single minisatellite region or hypervariable locus and which is homologous therewith to a degree enabling hybridisation of the nucleotide sequence to a corresponding DNA fragment containing a minisatellite from said single minisatellite region or hypervariable locus, detecting hybridised fragments of DNA, and comparing the hybridised fragments with a said control or controls, wherein:

1) said minisatellite region or hypervariable locus has an allelic variation of at least 3(100) and
2) said region or locus is detectable by a polynucleotide probe capable of differentiating DNA by reference to more than one polymorphic minisatellite region or hypervariable locus.

The present invention also relates to a corresponding method of characterizing a test sample in which the aforesaid region or locus has a degree of polymorphism of at least 3 as opposed to an allelic variation of at least 3.

The method of the present invention is preferably effected by the use of a polynucleotide or a polynucleotide preferred by a method of the present invention or a polynucleotide probe of the invention as hereinbefore defined.

Preferably the sample DNA is human DNA.

In order to assist the reader in following the present specification:

Hypervariable

A region of human, animal or plant DNA at a recognised locus or site is said be hypervariable if it occurs in many different forms e.g. as to length or sequence.

Minisatellite

A region of human, animal or plant DNA which is comprised of tandem repeats of a short DNA sequence. All repeat units may not necesarily show perfect identity.

Polymorphic

A gene or other segment of DNA which shows variability from individual to individual or between a given individuals paired chromosomes is said to be polymorphic.

Repeat or Tandem Repeat (Sequence)

A polynucleotide sequence which is perfectly or imperfectly repeated in series. In general a sequence which is said to be tandemly repeated will be repeated at least three times.

Imperfect Repeat (Sequence)

A sequence which is not an exact repeat either as to number or kind of nucleotides but recognizably a repeat of a consensus sequence.

% Homology

In comparing two repeat or tandem repeat sequences A and B, the percentage homology is given by the number of base pairs in A less the number of base pair substitutions, additions or deletions in B which would be necessary in order to give A, expressed as a percentage. Thus the percentage homology between two sequences ATGC and AGC is 75%.

Consensus Core (Sequence)

A sequence which can be identified as the closest match among a number of repeat sequences; usually among the repeat units of two or more different minisatellites.

Nucleotide (nt) and base pair (bp) are used synonymously. Both can refer to DNA or RNA. The abbreviations C, A, G, T refer conventionally to (deoxy)cytidine, (deoxy)adenosine, (deoxy)guanosine and either deoxythymidine or uridine. It will be appreciated however that the abbreviations A, C, G and T may include other base modified nucleosides capable of base pairing with one of the conventional nucleosides (deoxy)adenosine, (deoxy)cytidine, (deoxy)guanosine and either deoxythymidine or uridine. Such base modified nucleoside include (deoxy) inosine and (deoxy)8-azaguanosine.

Where the polynucleotide or polynucleotide probe of the present invention comprises a tandemly repeated sequence, the tandem repeats may be perfect repeats or imperfect repeats or a mixture of perfect and imperfect repeats. There are preferably at least three repeats and more preferably at least 7 repeats in the probe sequence.

The probes of the invention which may be used singly or in combination with other locus specific probes either in a sequence of tests or in a single test using a mixture or cocktail of probes may be useful in the following areas:

1. Paternity and maternity testing in man.
2. Family group verification in e.g. immigration disputes and inheritance disputes.
3. Zygosity testing in twins.
4. Tests for inbreeding in man.
5. General pedigree analysis in man.
6. Identification of loci associated with genetic disease in man, thereby enabling specific probes to be constructed to detect a genetic defect.
7. Forensic medicine, for example
   (a) fingerprinting semen samples from rape victims
   (b) fingerprinting blood, hair and semen samples from e.g. soiled clothing
   (c) identification of human remains.
   (d) charaterisation of other forensic tissue samples e.g. skin.
8. Cell Chimaerism studies, e.g. following donor versus recipient cells after bone marrow transplantation.
9. Livestock breeding and pedigree analysis/authentication. (This could include, for example, the routine control and checking of pure strains of animals, and checking pedigrees in the case of litigation involving e.g. race horses and dog breeding). Also to provide genetic markers which might show association with inherited traits of economic importance.
10. Routine quality control of cultured animal or plant cell lines, checking for contamination of pure cell lines and for routine identification work.
11. Analysis of tumour cells and tumours for molecular abnormalities.

12. It is anticipated that the polynucleotides or probes derived therefrom have a potential use in plant breeding. The locus specific probes of the present invention are, however, particularly useful in forensic medicine as demonstrated in Example 3 hereinafter and at least the probe pλg3 may cosegregate with the heterocellular form of hereditary persistence of foetal haemoglobin. The probes also provide a powerful method for use in paternity testing and related utilities (see utilities 2 and 5 above) as well as in cell chimaerism studies.

BRIEF DESCRIPTION OF THE DRAWINGS

FIG. 1A shows gel electrophoretic purification of a specified hypervariable DNA fragment from a DNA fingerprint, the fragment being designated therein as "fragment g". FIG. 1B shows the organization of DNA fragment g by means of a restriction map of cloned DNA;

FIG. 2 shows the DNA sequence of hypervariable fragment g, particularly highlighting the consensus repeat sequence and its alignment with the "core" sequence of British Patent Publication No. 2,166,445;

FIG. 6 shows the consensus repeat sequence units of the λMS series of minisatellites and of the pλg3 minisatellite;

Figure 3:
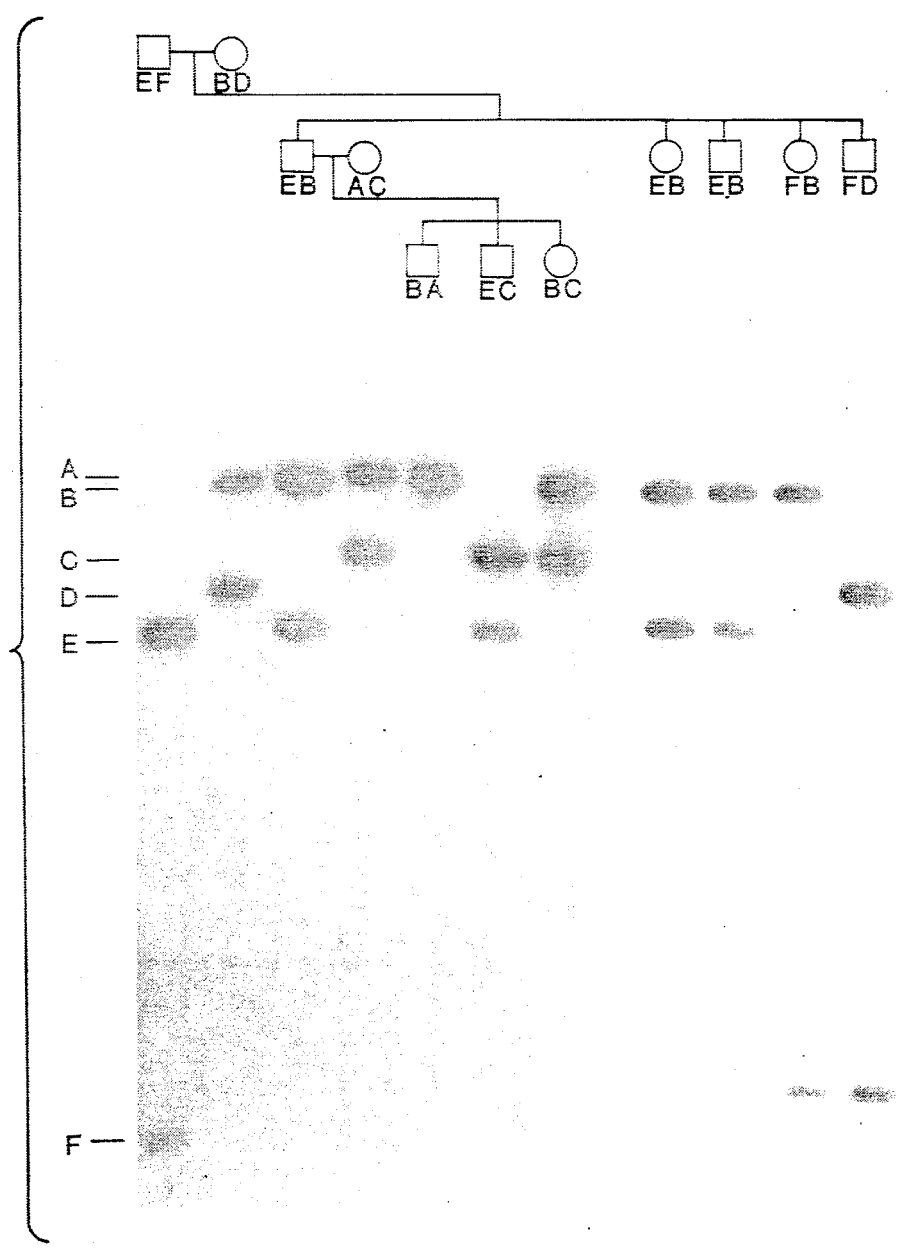
FIG. 3 shows the Mendelian inheritance of polymorphic DNA fragments detected by pλg3.

Advantageously the polynucleotides of the invention, and the polynucleotides prepared by the processes of the invention and polynucleotide probes of the present invention are capable of hybridizing with fragments of DNA containing a minisatellite from a minisatellite region or hypervariable locus which is identifiable by a polynucleotide probe comprising of any one sequence selected from:

| | |
|---|---|
| AGGAATAGAAAGGCGGGYGGTGTGGGCAGGGAGRGGC | 3 |
| GTGGAYAGG | 4 |
| TGGGAGGTGGRYAGTGTCTG | 5 |
| GAATGGAGCAGGYGRCCAGGGGTGACTCA | 6 |
| GGGCTGGGGAGATGGTGGAGGAGGTGTTGG | 7 |
| AGGCTGGGGAGATGGTGGAGGAAGAGTAC | 8 |
| TCTGTGTAATGGGTATAGGGAGGGCCCCGGGAAGGGGGTGTGGYX | 9 |

(wherein Y is C, T or U, X is G or C, R is A or G and T is T or U) or tandem repeats thereof; or a sequence complementary thereto.

The polynucleotides of the invention, polynucleotides prepared by the processes of the invention and probes of the present invention are capable of hybridizing with fragments of DNA containing a minisatellite from a single specific minisatellite region or hypervariable locus and are thus locus specific. In general the polynucleotides and probes of the present invention will be locus specific under high stringency hybridization conditions. In this regard the expression "locus specific" is used herein in relation to a polynucleotide or probe to mean that the polynucleotide or probe may be used under hybridization conditions which ensure that the polynucleotide or probe hybridizes to only a single specific locus.

It will be appreciated, however, that the locus specific probes of the present invention when used at reduced hybridisation stringencies may be capable of differentiating DNA by reference to more than one polymorphic minisatellite region or hypervariable locus and may thus be used to identify other informative genetic loci.

Thus according to a further feature of the present invention there is provided a method of preparing a polynucleotide capable of hybridizing to a DNA fragment which contains a minisatellite which is specific as to a particular region or locus in the genome, said region or locus having an allelic variation (as herein defined) of at least 3(100), which method comprises cloning a DNA fragment identified by hybridisation of fragments of genomic DNA with a polynucleotide probe as hereinbefore defined and preparing therefrom a polynucleotide capable of hybridizing to a DNA fragment which contains a minisatellite which is specific as to a particular region or locus on the genome, said region or locus having an allelic variation (as herein defined) of at least 3(100);

the method being effected under hybridisation conditions effective to render the probe capable of differentiating DNA by reference to more than one polymorphic minisatellite region or hypervariable locus.

According to a further feature of the present invention there is provided a polynucleotide, in isolated or cloned form, which comprises a nucleotide sequence which is specific as to a single minisatellite region or hypervariable locus and which is homologous therewith to a degree enabling hybridisation of the nucleotide sequence to a corresponding DNA fragment obtained by fragmenting sample genomic DNA with a restriction endonuclease, the said DNA fragment containing a minisatellite from said minisatellite region or hypervariable locus, wherein:

1) said region or locus has an allelic variation (as herein defined) of at least 3(100) and 2) said region or locus is detectable by a locus specific polynucleotide probe as hereinbefore defined.

The invention also relates to a corresponding method and to a corresponding polynucleotide in which the said region or locus has a degree of polymorphism of at least 3.

The invention further relates to probes comprising such locus specific polynucleotides and to a method of characterizing a test sample of DNA using such polynucleotides and polynucleotide probes.

The locus specific polynucleotides and probes of the present invention may be homologous with the minisatellite of the minisatellite containing DNA fragment or less preferably with a sequence flanking the minisatellite.

Where the polynucleotides and probes of the present invention comprise tandem repeats of a particular sequence such sequence will in general be repeated at least 3 times and such repeats need not necessarily be exact repeats. Repeats which are not exact are described elsewhere as imperfect repeats. Such repeats will nevertheless be recongizably repeated. In general this will mean that there is on average at least 70% homology between all repeating units. Preferably there is at least 80%, more preferably at least 85%, especially 90% homology between all repeating units. It will be appreciated however that the nucleotide sequence or "repeat unit" need not be repeated at all if desired.

The number of repeat units, n, is advantageously at least 5, but preferably at least 10. Conveniently n is 10 to 40, but in principle n can be any number, even from 1 up to 10,000.

Where the polynucleotides and probes of the present invention comprise tandem repeats of a particular sequence, any flanking sequences are largely irrelevant. They can be omitted or can be present in any number of nucleotides, for example up to 50,000 although to work with such a long probe would not ordinarily be sensible. Such large polynucleotides may nevertheless serve as carriers from which smaller polynucleotides, especially useful as probes, may be excised. These flanking sequences may form part of either ds-DNA or ss-DNA, even when the repeat sequences are of ss-DNA.

Preferably the polynucleotides and polynucleotide probes of the present invention comprise any one sequence selected from formulae 3 to 9 as hereinbefore defined or a sequence complementary thereto or tandem repeats thereof (there being on average at least 70% homology between all tandemly repeated sequences) or a sequence complementary thereto.

One preferred polynucleotide of the present invention thus comprises the sequence of formula 3 as hereinbefore defined or tandem repeats thereof or a sequence complementary thereto. Such a nucleotide sequence is specific as to an autosomal locus located on chromosome 7.

Polynucleotides and polynucleotide probes comprising such a sequence are referred to herein as pλg3.

A further preferred polynucleotide of the present invention comprises the sequence of formula 4 as hereinbefore defined or tandem repeat(s) thereof or a sequence complementary thereto. Such a nucleotide sequence is specific as to a locus located on chromosome 1. Polynucleotides and polynucleotide probes comprising such a sequence are referred to herein as λMS1.

A further preferred polynucleotide of the present invention comprises the sequence of formula 5 as hereinbefore defined or tandem repeat(s) thereof, or a sequence complementary thereto. Such a nucleotide sequence is specific as to a locus located on chromosome 7. Polynucleotides and polynucleotide probes comprising such a sequence are referred to herein as λMS31.

A further preferred polynucleotide of the present invention comprises the sequence of formula 6 as hereinbefore defined or tandem repeat(s) thereof or a sequence complementary thereto. Such a nucleotide sequence is specific as to a locus located on chromosome 1. Polynucleotides and polynucleotide probes comprising such a sequence are referred to herein as λMS32.

A further preferred polynucleotide of the present invention comprises a sequence selected from formulae 7 and 8 as hereinbefore defined or tandem repeat(s) thereof or a sequence complementary thereto. Such a nucleotide sequence is specific as to a locus located on chromosome 5. Polynucleotides and polynucleotide probes comprising such sequences are referred to herein as λMS8.

A further preferred polynucleotide of the present invention comprises the sequence of formula 9 as hereinbefore defined or tandem repeat(s) thereof or a sequence complementary thereto. Such a nucleotide sequence is specific as to a locus located on chromosome 12. Polynucleotides and polynucleotide probes comprising such a sequence are referred to herein as λMS43.

As indicated above there is in general at least 70%, advantageously at least 80%, preferably at least 85% and most preferably at least 90% homology between repeat units. It is especially preferred however that any one of the sequences of formulae 3 to 9 be repeated exactly. In this regard it will be appreciated that this latter requirement may be met provided that each repeat unit has a sequence falling within the scope of the desired formula; it is thus not necessary that each repeat unit possesses exactly the same sequence.

In a preferred embodiment of the present invention there is provided a method of establishing the identity or otherwise of the test sample donor with one or more control sample donors, in which the control sample(s) are similarly fragmented and a comparison is made of the hybridized fragments from the respective samples.

In a further preferred embodiment there is provided a method of establishing a family connection between the test sample donor and one or more control sample donors, in which the control sample(s) are similarly fragmented and a comparison is made of the hybridized fragments from the respective samples.

The above-mentioned methods may be effected using the polynucleotides or probes of the present invention either singly or by using at least two polynucleotides or probes of the present invention either in a sequence of tests or in a single test using a mixture of the said polynucleotides or probes.

In a further preferred embodiment of the present invention there is provided a method for the diagnosis of an inherited disease, abnormality or trait which comprises probing the test sample with at least one polynucleotide or polynucleotide probe as hereinbefore defined, said probe, being associated with a particular inherited disease, abnormality or trait.

The probes of the present invention which we have tested all serve as locus-specific probes under high stringency hybridization conditions.

The extreme variability of loci detected by those probes of the present invention which we have tested, combined with their sensitivity in Southern blot hybridizations, provide an especially useful tool in individual identification, particularly when insufficient DNA is available for multi-locus DNA fingerprinting analysis as described and claimed in British Patent Application No. 8525252 (Publication No. 2,166,445); multi-locus DNA fingerprints can be obtained from 0.5 μg DNA, whereas the locus-specific probes are at least an order of magnitude more sensitive and can be used on as little as 1 μl blood.

In any unusual situation where even smaller quantities of sample might require testing then the present invention will be particularly valuable in conjunction with the amplification technique described in European Patent Application No. 86302299.2 (Publication No. 0201184).

The present invention enables informative genetic loci to be identified in the human genome and thereby enables locus specific probes to be prepared, each locus specific probe being specific as to a single informative genetic locus. We have specifically identified six different very informative genetic loci, which loci possess very high heterozygositites in the population tested (at least 90%) and which are amongst the most polymorphic so far isolated and we have prepared a locus specific probe for each locus which probes we have designated pλg3, λMS1, λMS8, λMS31, λMS32 and λMS43 (as hereinbefore defined).

The degree of individual specificity of genotypes determined by locus-specific probes can be estimated from the heterozygosity H at each locus. The mean allele frequency q at a locus is given by (1-H), and the probability that two randomly-selected individuals share the same genotype is $q^2(2-q)$. This probability of false association of two individuals varies from 0.02 for λMS8 ot 0.0002 for λMS31, and is a conservative estimate in that heterogeneity in q will reduce these probabilities. The cumulative probability of false association for all six minisatellite probes is $\neq 10^{-16}$, comparable to the odds that two randomly-selected DNA fingerprints detected by one multilocu probe are identical (see British Patent Application No. 8525252). In contrast, the chance that two sibs are identical for a given hypervariable locus is given by $\frac{1}{4}(1+q)^2$. The cumulative probability of sib identity for all six probes is 0.0004, compared with $\sim 10^{-7}$ for a DNA fingerprint using one multilocus probe.

Figure 11A:
FIG. 11 shows an assessment of the sensitivity of locus specific hypervariable probes and their application to the forensic analysis of a double rape/murder case.
Figure 11C:
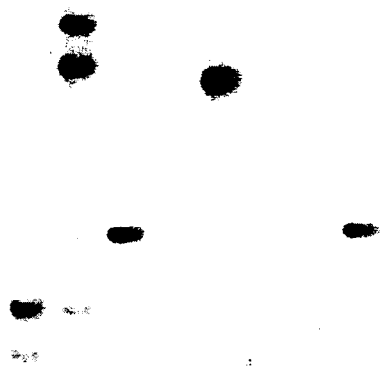

These locus-specific hypervariable probes should prove particularly useful in forensic medicine, as shown by the murder case analysed in FIG. 11C where insufficient DNA was recovered from two of the forensic samples for DNA fingerprint analysis. Semen DNA from both victims showed a common phenotype with probes λMS1 and λMS31 different from that of the suspect. From the above discussion, we can calculate the probability that victims X and Y had been sexually assaulted by different unrelated men at $2\times10^{-7}$. Similarly, the chance that the two hypothetical assailants were first-degree relatives, for examples brothers, is 0.07. This provides strong evidence that X and Y were sexually assaulted by the same man, a conclusion which was subsequently confirmed by DNA fingerprint analysis of larger amounts of forensic material. Furthermore, the semen stains from X and Y are almost certainly derived from a single individual, rather than two or more assailants. Consider for example stain b in FIG. 11C, which shows two victim alleles and two additional assailant alleles. The chances that a pool of three individuals (two assailants and one victim) would show four or less resolvable alleles is given by $q^2(55-210q+216q^2)$. For probe MS1, this probability is 0.02 and for probe λMS31 0.005, giving a combined probability that X was sexually assaulted by two men, rather than one, of $10^{-4}$. This establishes that X and Y were assaulted by a single individual, and shows that locus-specific probes, unlike multi-locus DNA fingerprint probes, can be used to estimate the number of individuals represented in a mixed DNA sample.

The Mendelian inheritance of the hypervariable DNA fragments also allows them to be used for establishing family relationships in for example paternity disputes. For a given locus-specific probe, the probability that a child's paternal allele is fortuitously present in a randomly-selected man can be estimated at $2q-q^2$. For all six minisatellites, the cumulative probability of false inclusion of a non-father is $$\prod_{1}^{6}(2q_i - q_i^2) = 10^{-7},$$

comparable to that obtained using two DNA fingerprint probes. Similarly, the cumulative probability of false inclusion of a first degree relative of the true father, such as a brother, is 0.02. Thus sequential use of these hypervariable locus-specific probes can provide a powerful method for establishing family relationships with the caveat that mutations to new length alleles at these unstable loci could occasionally lead to false exclusions. The mutation rate at these hypervariable loci is not yet known.

Figure 12:
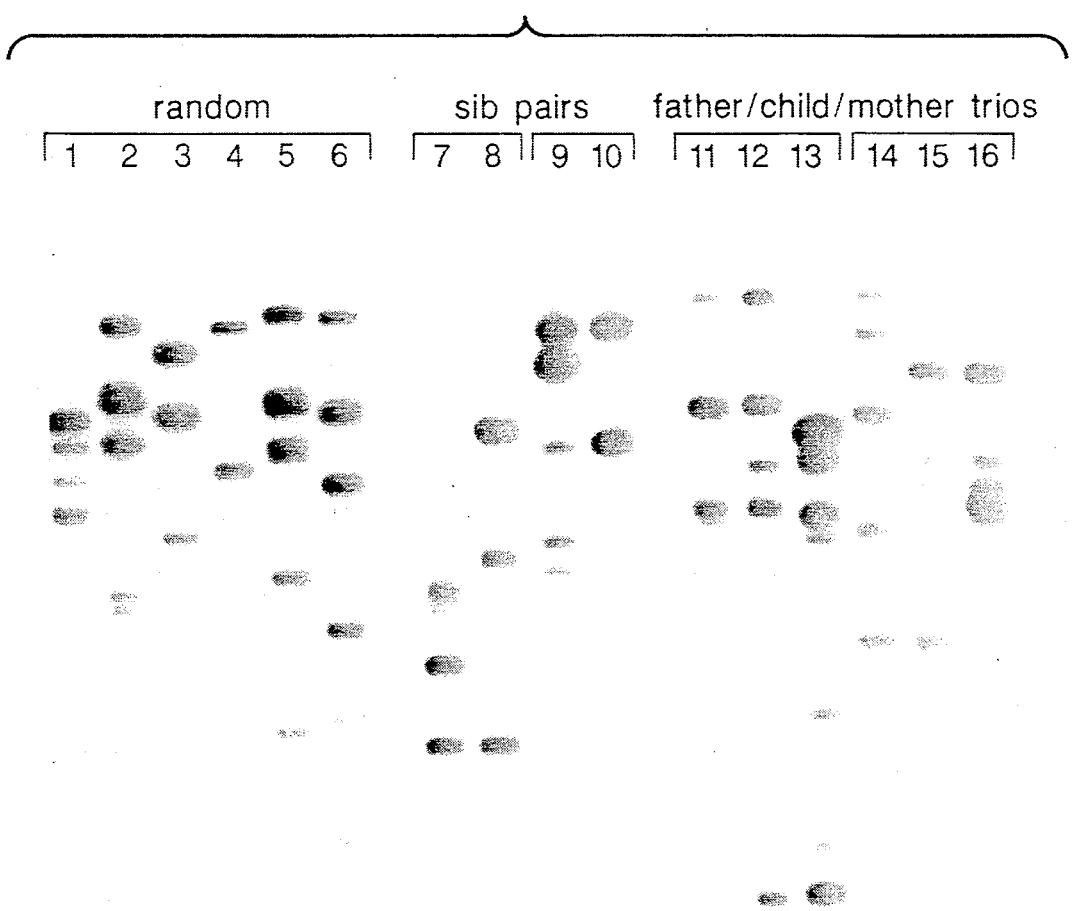
FIG. 12 shows the detection of multiple hypervariable loci in human DNA by hybridisation with pooled minisatellite probes of the present invention.

The locus-specificity and sensitivity of these locus-specific probes enable pooled probes to be used to generate multi-locus Southern blot patterns (FIG. 12). These "reconstituted DNA fingerprints" produced by 5 pooled probes are considerably less complex than their counterparts detected by multi-locus probes, and should be more amenable to being encoded digitally following densitometric scanning. Despite the high variability of the individual minisatellites, the pooled-probe profiles show a substantial (18%) level of fragment sharing between unrelated North European individuals, mainly as a result of electrophoretic comigration of minisatellite fragments from different loci. This level of band sharing is similar to that seen in conventional DNA fingerprints produced by multi-locus probes, where the level of band sharing is ~25% between randomly-selected individuals. Since on average 8.4 DNA fragments are resolved in a mixed-probe pattern, the chance that all of these fragments in one individual are present in a second randomly-selected individual can be conservatively estimated at $0.18^{8.4}=6\times10^{-7}$. These patterns therefore provide a high level of individual specificity, though not as high as can be achieved using multi-locus probes or by sequential hybridization with locus-specific probes (see above). Both the pooled probes and individual locus-specific probes will prove particularly useful in studies of cell chimaerism, particularly for providing donor versus recipient markers for following engraphment after bone marrow transplantation; DNA mixing experiments (FIG. 12) indicate that low levels of chimaerism could be detected using these probes.

In the following Examples temperatures are given in °C. and the probes 33.6 and 33.15 are as described in British Patent Publication No. 2,166,445 having the consensus repeat sequence:

(A)AGGGCTGGAGG, and

AGAGGTGGGCAGGTGG respectively

EXAMPLE 1

This Example describes the isolation and properties of a specified minisatellite fragment in a DNA fingerprint.

General methods

DNA was isolated from white blood cells as described by Jeffreys A J et al, (1985) Nature 316, 76–79 and from an Epstein Barr virus transformed lymphoblastoid cell line (see Nilsson, K et al (1971) Int. J. Cancer 8, 443-450) derived from individual III 9 of the HPFH pedigree described by Jeffreys et al., Am. J. Hum. Genet. 39, 11-24. Restriction digestion and Southern blot hybridizations were performed as described elsewhere in the above-mentioned references of Jeffreys A J et al. Double-stranded DNA probe fragments were isolated by electrophoresis onto DE81 paper as described by Dretzen, G et al (1981) Anal. Biochem. 112, 295-298 and labelled with $^{32}P$ by random oligonucleotide priming as described by Feinberg, A P et al (1984) Anal. Biochem. 137, 266-267; single-stranded minisatellite probe 33.15 was prepared as described by Jeffreys et al (1985) Nature 314, 67-73.

Cloning hypervariable fragment g

600 μg individual III 9 lymphoblastoid cell line DNA digested with Sau3A was fractionated by electrophoresis through a 0.5% agarose gel, and relevant size fractions collected by electroelution onto dialysis membrane as described in Yang, R C A et al, (1979) Meth. Enzymol, 68, 176-182. After two cycles of preparative gel electrophoresis fragment g was 1000 fold purified (yield 150 ng DNA). 20 ng of this partially purified fraction was ligated to 60 ng λL47.1 arms isolated after cleavage with BamHI (see Loenen, W A M and Brammar, W J (1980) Gene. 20, 249-259) packaged in vitro and plated onto E. coli WL95 (803, supE, supF, hsdR$_k$-, hsdM$_k$+, tonA, trpR-, metβ, lysogenic for P2) [see Loenen reference above and Jeffreys, A J et al (1982) J Mol. Biol. 156, 487-503] to select for recombinants. The resulting library of 1500 recombinant phage was screened by plaque hybridization with minisatellite probe 33.15. Four positive plaques were replated and rescreened on E. coli ED8910 (803, supE, supF, recB21, recC22, hsdS) [see Loenen reference above] and recombinant phage DNA prepared by the method of Blattner et al (1977) Science 194, 161-169. The Sau3A insert of recombinant phage g3 was subcloned into the BamHI site of pUC13 [Vieira J and Messing J (1982) Gene 19, 259-268] and propagated in a recA derivative of E. coli JM83 JM83, Δ (recA-sr1R) 306::Tn10 [see Matfield, M (1983) Ph.D. thesis, University of Leicester].

DNA sequence analysis pλg3 DNA was sonicated, size-selected and shotgun cloned into the Sma I site of M13mp19 [see Yanis-Perron C et al (1985) Gene 33, 103-119]. To determine the DNA sequence of the tandem-repetitive region of pλg3, 12 random clones were sequenced by the dideoxynucleotide chain-termination method [see Sanger, F et al (1977) Proc. Nat. Acad. Sci. USA 74, 5463-5467 and Biggin M D et al (1983) Proc. Natl. Acad. Sci. USA 80, 3963-3965]. 8 of these clones were derived from the tandem-repetitive minisatellite region of pλg3 and were used to define the consensus repeat sequence. M13 clones containing the 5' and 3' flanking regions were detected by hybridization with $^{32}P$-labelled flanking probes a and b (see FIG. 1 described below) and sequenced to establish the flanking region sequence and the beginning and end points of the minisatellite.

RESULTS

Isolation of a specific minisatellite from a DNA fingerprint

Individual III9 from the Gujarati pedigree described by Jeffreys et al. [(1986) Am. J. Hum. Genet. 39, 11-24] is affected by HPFH (hereditary persistance of foetal haemoglobin) and her DNA fingerprint, detected in Sau3A digest by minisatellite probe 33.15, contains a 8.2 kb polymorphic fragment (fragment 'g'; FIG. 1A) which tends to cosegregate with HPFH in other members of this pedigree as described in (1986) Am. J. Hum. Genet. 39, 11-24. This DNA fragment was purified away from other minisatellite fragments by two rounds of preparative gel electrophoresis (FIG. 1).

FIG. 1 illustrates this purification by gel electrophoresis. DNA from individual III9 in the pedigree described by Jeffreys et al was digested with Sau3A and 6-9 kb fragments collected by preparative gel electrophoresis (fraction 1). These fragments were re-electrophoresed to give fractions 2-5. Aliquots of III9 DNA digested with Sau3A and of each fraction were electrophoresed through a 0.8% agarose gel and Southern blot hybridized with the minisatellite probe 33.15. Fragment g (8.2 kb), which tends to cosegregate with HPFH, is approximately 1000-fold purified in fraction 3.

The fragment 'g', detected in the Sau 3A digest referred to above, and purified as described to produce an approximately 1000 fold enriched fragment 'g' fraction was cloned into λL47.1 as described in the above-mentioned Loenen and Brammar reference, and propagated on P2 lysogenic rec+ E. coli to select for recombinant phage. The resulting library was screened by hybridisation to probe 33.15. The four positive plaques obtained were very small (plaques <0.1 mm diameter) but could be replated at a low efficiency 0-8 pfu/plaque) on recB, recC E. coli to produce normal-sized plaques (1 mm diameter). Two clones, λg1 and λg3, were further characterized and shown to contain a Sau3A insert of 7.7 and 7.8 kb repectively. These clones were both derived from band g (see below), but were shorter than band g by 0.5 and 0.4 kb respecively. Since there was no size heterogeneity of the Sau3A insert in either λg1 or λg3 grown on recB, recC E. coli (data not shown), we conclude that part of the insert has been lost from each clone during their initial propagation in rec+ E. coli.

Yields of λg1 and λg3 DNA prepared by the Blattner method [see (1977) Science 194, 161-169] were very low (1% of the normal yields of λL47.1 recombinant DNA), again pointing to abnormal growth properties of these minisatellite clones. The Sau3A insert was therefore subcloned into pUC13 [see Vieira, J and Messing J (1982) Gene 19, 259-268] and propagated in a recA derivative of E. coli JM83 [see Matfield M (1983) Ph.D thesis University of Leicester] to minimise rearrangement of the insert. The resulting subclone, pλg3 (see FIG. 1B described below), contained a 7.1 kb Sau3A insert, 0.7 kb shorter than the insert in g3.

Organisation of minisatellite fragment g

The structure of the minisatellite fragment in pλg3 was determined by restriction mapping (FIG. 1B) and DNA sequencing (FIG. 2).

FIG. 1B shows the organization of DNA fragment g. The Sau 3A insert in pλg3 was mapped with restriction endonuclease AluI (A), DdeI (D), Hae III (H) MboII (M), PstI (P) and Sau3A (S). There are no cleavage sites for HinfI or RsaI. The 7.14 kb insert contains 171 tandem repeats of a 37 bp sequence (see FIG. 2) plus 747 bp flanking DNA. The 5' flanking region contains the beginning of an inverted Alu element (hatched). The origins of unique sequence flanking probes a and b are shown.

FIG. 2 shows the DNA sequence of hypervariable fragment g. The sequence of the 5' and 3' flanking regions and the beginning and end of the minisatellite is shown together with the repeat sequences of three random regions (a–c) from the minisatellite. The beginning of the inverted Alu element is shown in underlined uppercase, and several simple sequence regions in the 5' flanking region are underlined. The consensus sequence (con) of the 37 bp minisatellite repeat unit is shown, and differences from this consensus are given for individual repeat units. The second repeat unit in region c contains a HaeIII cleavage site (underlined), and this region therefore spans the internal HaeIII site in the minisatellite (FIG. 1B). The consensus repeat sequence is also shown aligned with the "core" sequence in a similar manner to that in British Paent Publication No. 2,166,445.

The clone pλg3 contains a 6.3 kb minisatellite devoid of restriction sites, except for a single internal HaeIII site. The minisatellite is comprised of 171 repeats of a 37 bp unit which contains the sequence GTGGGCAGG; this sequence corresponds precisely to the most invariant part of the 11-16 bp core sequence previously identified as being shared by several different human minisatellites (see British Patent Publication No. 2,166,445 and FIG. 2 herein). The repeat units are not completely homogeneous; sequence analysis of several randomly-selected regions from within the minisatellite revealed a limited amount of repeat sequence variation. Most variants, including a 4 bp deletion which produces a subset of 33 bp repeat units, are diffused over more than one repeat unit. One variant (an A→C transversion in region C) creates the unique internal HaeIII site and is therefore probably only found in one repeat unit. The beginning and end repeat units of the minisatellite are noticeably more diverged in sequence than are internal repeats.

The minisatellite in pλg3 is flanked by nonrepeated DNA containing the normal density of restriction sites (FIG. 1B). The beginning of the 5' flanking region is comprised of the head of an inverted Alu element. The remaining 5' and 3' flanking regions, defined by hybridization probes a and b (FIG. 1B), are unique sequence DNA and hybridize only to this locus in the total DNA (data not shown). The 5' flanking region contains a considerable amount of simple sequence DNA [polypurine and $(ACC)_n$] (FIG. 2).

Minisatellite fragment g detects a single polymorphic locus

To determine whether the entire cloned minisatellite fragment can be used as a hybridization probe to detect specifically the corresponding locus in human DNA, the Sau3A insert from pλg3 was hybridized in the presence of human competitor DNA to human DNA digested with HinfI, the restriction enzyme routinely used for DNA fingerprinting (FIG. 3).

FIG. 3 shows the Mendelian inheritance of polymorphic DNA fragments detected by pλg3. 8 µg samples of human DNA were digested with HinfI and electrophoresed through a 0.8% agarose gel. Digests were Southern blot hybridized with the Sau3A insert of pλg3, in 1×SSC at 65° in the presence of 6% polyethylene glycol and 50 µg/ml alkalisheared human placental competitor DNA, and washed after hybridization in 0.2×SSC at 65°. pλg3 detects a single locus which is heterozygous in all individuals shown. Inheritance of alleles (indicated by letters) is Mendelian.

At high stringencies (0.2×SSC, 65°), either one or two hybridizing fragments were detected in all individuals examined. pλg3 detected the 8.2 kb fragment g in previously-tested relatives of III 9, confirming that band g had been cloned (data not shown). At lower stringencies (1×SSC, 65°), additional faintly hybridizing polymorphic DNA fragment were detected (data not shown).

DNA fragments detected by pλg3 at high stringencies segregate in a Mendelian fashion as alleles of a single locus (FIG. 3). This locus is not sex-linked and also showed no significant but incomplete sex-linkage in two large pedigrees studied (61 progeny tested, $\hat{z}=0.18$ at $\hat{\theta}=0.43$; data not shown); it therefore behaves as an autosomal locus, and has been located on chromosome 7 (see Table 1).

Extreme polymorphic variation at this minisatellite locus

Figure 4:
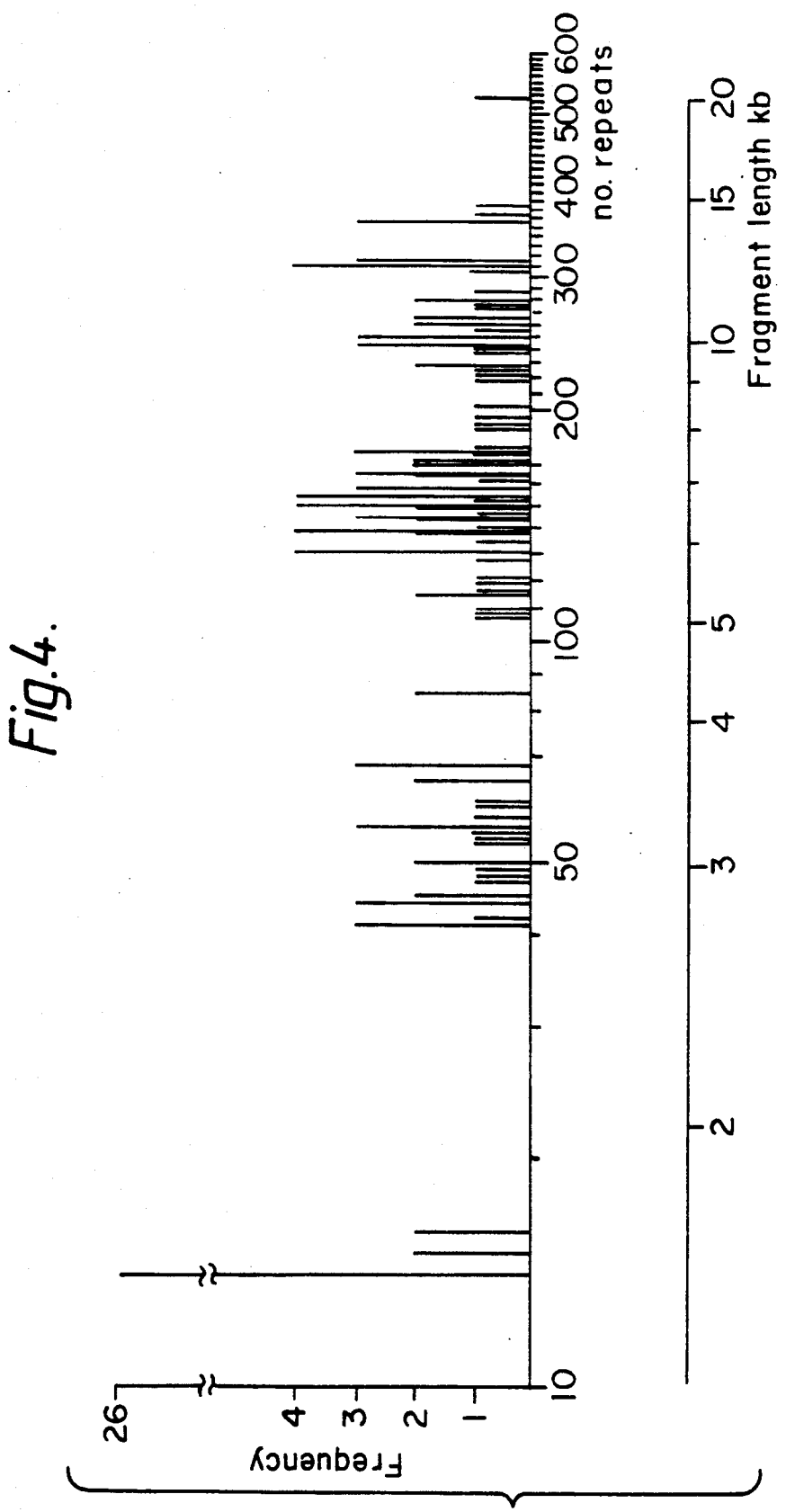
FIG. 4 shows the distribution of minisatellite allele sizes detected by hybridisation to pλg3.

HinfI digests of DNA from 79 randomly-selected British caucasians were screened with the insert from pλg3, first singly and then in pools of 14 people (1 µg DNA per individual) which were electrophoresed though a 35 cm long 0.7% agarose gel to maximise allele resolution. The lengths of the different alleles detected in this population sample are shown in FIG. 4, together with the estimated number of repeat units in each allele and the allele frequencies. Thus FIG. 4 shows the distribution of minisatellite allele sizes. The length of the minisatellite in the shortest common allele was determined by genomic mapping of this fragment in a homozygote, using flanking single-copy probes a and b (FIG. 1) (data not shown). The number of repeats per allele is approximate and depends on the ratio of 37 to 33 bp repeat units in the minisatellite. Excluding the short common allele, the remaining alleles were sampled either once (42 alleles), twice (12 alleles), three times (12 alleles) or four times (5 alleles). This distribution does not differ significantly from that predicted if all of these alleles are uniformly rare (q=0.0081, $^2$[4 d.f.]=4.0), and is therefore consistent with a simple model of one common short allele (q=0.165) and 103 equally rare alleles (q=0.0081 per allele) being present in the population.

At least 77 different alleles could be resolved in this population sample, with repeat numbers ranging from 14 to ~525 per allele. The homozygotes in the population sample were all homozygous for the shortest allele. The above estimates of number of alleles and the mean frequency of rare alleles are limited by gel resolution, and the true number of different length alleles in this sample may be greater.

The distribution of allele lengths does not appear to be completely random, but shows evidence of trimodality (FIG. 4), with short (14–16 repeats), medium (41–68 repeats) and long (107–525 repeats) classes of alleles. A bimodal distribution of allele lengths has been previously noted in caucasians for the hypervariable region located 5' to the human insulin gene [see Bell, G I et al (1982) Nature 295, 31–35], though this bimodality is not evident in blacks [Lebo, R V et al (1983) Proc. Nat. Acad. Sci. USA 80, 4804–4812].

The isolation of fragment g demonstrates that the large and highly polymorphic DNA fragments in DNA fingerprinting are in principle amenable to molecular cloning to provide locus-specific probes suitable for studying individual hypervariable regions. While fragment g could be cloned in bacteriophage λ, the resulting clones showed abnormal growth properties on rec+ E. coli. This will lead to a depletion of minisatellite clones from conventional amplified human libraries in phage. The cloned minisatellite is unstable both in and on subcloning into pUC13 in recA. E. coli; the final recombinant pλg3 had lost about 30 repeat units compared with fragment g. The physical map of pλg3 (FIG. 1) does not therefore completely reflect the organization of fragment g.

The cloned DNA fragment has the structure expected for a minisatellite, establishing that fragment g is not derived from a longer satellite DNA. Despite the presence both of a "core" sequence in each repeat unit and part of an Alu sequence in the 5' flanking region, the cloned fragment g acts, in the presence of competitor human DNA, as a locus-specific probe. The failure of pλg3 to detect efficiently other core-containing minisatellites is due to the additional non-core DNA present in each repeat unit which probably interferes with cross-hybridization to other minisatellites (see British Patent Publication No. 2,166,445).

The cloned minisatellite shows extreme length polymorphism, presumably due to allelic variation both in the number of repeat units and in the ratio of 37 and 33 bp repeat types in each allele. In a random population sample of 158 chromosomes, one common and at least 76 rare alleles could be resolved. This locus is much more polymorphic than most or all of the cloned human hypervariable regions so far characterized including the selection of relatively short cloned minisatellites initially used to define the "core" sequence [see British Patent Publication No. 2,166,445]. The heterozygosity at this locus is at least 96.6%, with most homozygotes arising from the short common allele.

New alleles at this locus are generated by alteration in the repeat number, either by slippage during DNA replication or by unequal exchange driven by the "core" sequence, a putative recombination signal. Under the neutral mutation random drift hypothesis, the parameter $4N_e v$ ($\theta$), where $N_e$ is the effective population size and v is the mutation rate per gamete to a new length allele, can be most accurately estimated from the number of different alleles scored in a population sample, using the infinite allele model [see Ewens W J (1972) Theor. Popul. Biol. 3, 87–112]. We estimate $\theta$ at 60–90 for this locus, depending on whether the common short allele is included or not. Since $N_e$ for man is $\sim 10^4$, the mutation rate v to new length alleles at this locus is approximately 0.002 per gamete. This value of v is an underestimate, since the number of alleles detected is limited by gel resolution and since there is not an infinite number of potential resolvable alleles. The average length of minisatellite DNA at this locus is 5 kb, and thus the mutation (recombination) rate per kb minisatellite is $>4 \times 10^{-4}$, compared with $10^{-4}$ per kb estimated for other shorter core-containing minisatellites and a mean meiotic recombination rate of $10^{-5}$ per kb for human DNA [see Jeffreys, A J et al (1985) Nature 314, 67–73]. Thus the rate of generation of new alles at this minisatellite locus is remarkably high, consistent with the inventor's previous suggestions that these core-rich regions may be recombination hotspots. Presumably, the mutation rate is relatively low for short alleles, which might explain how the shortest allele has drifted to achieve a significant frequency in the population without being disrupted by unequal exchange during this process.

DNA fingerprints have proved a powerful method for individual identification and for establishing family relationships in for example paternity and immigration disputes. The accuracy of this method is determined by the low mean probability x that a band is shared by two randomly-selected individuals. For British caucasians, x has been estimated empirically at 0.2 for DNA fingerprint HincI fragments larger than 4 kb. In cases where band sharing between individuals occurs (that is, where a band in one individual is matched in a second individual by a band of similar mobility and autoradiographic intensity), it is not clear whether the shared bands represent identical alleles of the same minisatellite locus. The allele distribution in FIG. 4 enables us to calculate x for alleles >4 kb; for this specific minisatellite locus, x=0.016, an order of magnitude lower than the estimate from multi-locus DNA fingerprints. If this cloned minisatellite is typical of loci represented in DNA fingerprints, then most bands shared between unrelated DNA fingerprints are due to fortuitous comigration of different minisatellite fragments. The important practical consequence of this is that, in cases of non-exclusion in for example paternity disputes where all paternal bands in a child are precisely present in the DNA fingerprint of the putative father, the very low probability of false inclusion previously calculated for x=0.2 is a gross overestimate of the true probability (for x=0.016).

Using DNA fingerprint probes 33.6 and 33.15, it is possible to score the segration of up to 34 dispersed autosomal loci in large human sibships. For most loci examined, only one of the two alleles is scorable in the set of larger (>4 kb) resolved DNA fingerprint fragments, suggesting that large size differences exist between minisatellite alleles, with many alleles being located in the poorly resolved (<4 kb) region of the DNA fingerprint. This is also seen for the cloned minisatellite; HinfI alleles at this locus vary from 1.7 to 20.4 kb in length, and the allele frequency distribution in FIG. 4 shows that both alleles of this locus would be resolved in the DNA fingerprints of only 40% of individuals, while neither allele would be scorable in 14% of people.

Minisatellite probes 33.6 and 33.15 detect together about 60 hypervariable loci, many of which should now be amenable to cloning to provide a bank of highly informative single locus probes, for example ideal for linkage studies in man. Linkage analysis of inherited disorders is also possible in single large families using the entire DNA fingerprint. If a polymorphic fragment is detected which appears to cosegregate with the disease, it is essential that this fragment be cloned to provide a locus-specific probe for extending the linkage analysis to additional affected families.

In the following Example 2 below the materials and methods set out below were used.

a) Cloning a selection of large minisatellites

5 μg blood DNA from each of 40 randomly-selected individuals were pooled, digested to completion with Sau3A and 5-15 kb fragments isolated by preparative electrophoresis in a 0.6% agarose gel followed by electroelution onto a dialysis membrane. The purified fraction was electrophoresed in a second preparative gel to remove all traces of contaminating small Sau3A fragments. 50 ng of the 5-15 kb fraction were ligated to 100 ng λL47.1 arms isolated after cleavage with BamHI [Loenen and Brammar, (1980) Gene 20, 249-259] packaged in vitro and a library constructed, screened with human minisatellite probes 33.6 and 33.15 (see British Patent Publication No. 2,166,445) and positive plaques isolated as described in Example 1 to produce the MS series of recombinant phage.

b) Isolation of minisatellite hybridization probes

Recombinant phage DNA was digested with Sau3A and the large insert fragment separated from small vector fragments by electrophoresis in low gelling temperature agarose (Sea Plaque). The gel slice containing the insert was dissolved in 3 vol water at 65° and aliquots containing 10 ng insert DNA were labelled with $^{32}$P by random oligonucleotide priming [Feinberg and Vogelstein, (1984) Anal. Biochem. 137, 266-267.

c) Southern blot hybridization

Genomic DNA samples were restricted and electrophoresed as described by Jeffreys et al (1986) Am. J. Hum. Genet. 39, 11-24. DNA was transferred to Hybond-N (Amersham), fixed by u/v irradiation and prehybridized at 65° for 5 min in 0.5M sodium phosphate, 7% SDS, 1 mM EDTA (pH7.2) [Church and Gilbert, (1984), Proc. Natl. Acad. Sci. USA 81, 1991-1995. Filters were hybridized overnight with 0.5 μg/ml $^{32}$P-labelled probe DNA (specified activity ~$10^9$ cpm/ug DNA) in the presence of 25 μg/ml sheared single-stranded human placental DNA competitor. After hybridization, filters were washed at 65° in 40 mM sodium phosphate, 1% SDS (pH7.2) followed by a high stringency wash at 65° in 0.1×SSC (15 mM NaCl, 1.5 mM trisodium citrate pH7.0) 0.01% SDS. Filters were autoradiographed from 3 hr to 1 week at −80° in the presence of an intensifier screen.

d) Determination of the tandem repeat sequence of the MS recombinants

Each MS recombinant DNA was sonicated and 0.3-0.6 kb fragments size-selected and shotgun cloned into the SmaI site of M13mp19 [Yanis-Perron, Vieira and Messing, (1985), Gene 33, 103-119]. Recombinant phage were screened by plaque hybridization with $^{32}$P-labelled MS insert DNA. 10 strongly-positive single-stranded phage DNAs from a given MS recombinant were compared pairwise by the C-test [Winter and Fields, (1980) Nucleic Acids Res. 8, 1965-1974]; most DNAs fell into two complementary C-test groups and were therefore likely to be derived from the long, tandem-repetitive region of the λMS insert. Two M13 recombinants from each of the two complementary groups were sequenced by the dideoxynucleotide chain-termination method [Sanger, Nicklen and Coulson, (1977) Proc. Natl. Acad. Sci. USA 74, 5463-5467; Biggin, Gibson and Hong, (1983) Proc. Natl. Acad. Sci. USA 80, 3963-3965] to determine the consensus repeat sequence of each MS recombinant on both strands.

EXAMPLE 2 a) Isolation of a selection of locus-specific hypervariable DNA probes

The strategy for cloning a selected fragment from a human DNA fingerprint by preparative gel electrophoretic isolation of the fragment followed by cloning in bacteriophage has been described in Example 1. To isolate a wider range of minisatellites, 6-15 kb size-selected Sau3A fragments from DNA pooled from 40 randomly-selected individuals were cloned into the BamHI replacement vector λL47.1 [Leonen and Brammar, (1980): "A bacteriophage lambda vector for cloning large DNA fragments made with several restriction enzymes" Gene 20, 249-259]. Since human minisatellites can show substantial allelic variation in length, as demonstrated in Example 1, the use of pooled human DNAs to clone large Sau3A fragments should maximize the number of clonable hypervariable loci which have large Sau3A alleles. From a library of 2000 recombinants, 5 phage were isolated by hybridization to human minisatellite probe 33.15 and an additional 5 phage were detected by probe 33.6, to produce the MS series of recombinants (see Table 1).

TABLE 1

Summary of hypervariable locus-specific minisatellite probes

| Clone | detected by | other isolates | Sau3A insert length kb | variation detected with | heterozygosity % | allelic length range, kb | chromosome assignment |
|---|---|---|---|---|---|---|---|
| pλg3 | 33.15 | — | 7.1 | HinfI | 97 | 1.5-22 | 7q 31.3 qter |
| λMS1 | 33.15 | — | 4.6 | HinfI | 98 | 2.0-22 | 1p |
| λMS8 | 33.6 | MS40, M242 MS47 | 7.0 | HinfI | 90 | 2.4-9.5 | 5 |
| λMS31 | 33.15 | — | 5.7 | HinfI | 99 | 3.5-13 | 7pter q22 |
| λMS32 | 33.15 | — | 5.9 | AluI | 97 | 2.3-28 | 1q |
| λMS43 | 33.6 | — | 8.3 | HinfI | 94 | 3.5-16 | 12 |

To determine whether each λMS recombinant could act as a locus-specific probe for a hypervariable minis tellite, the Sau3A insert of each recombinant was hybridized in the presence of human competitor DNA to HinfI digests of three randomly selected individuals, or to AluI digests for λMS32, the minisatellite tandem repeat units of which contain a HinfI site (FIG. 5). 8 out of 10 of the recombinants hybridized to one or two large variable DNA fragments in each human DNA tested. Four of the recombinants detected by probe 33.6 (λMS8, 40, 42 and 47) hybridized to the same pattern of variable DNA fragments and are therefore derived from the same hypervariable locus (FIG. 5 Table 1).

Figure 5:
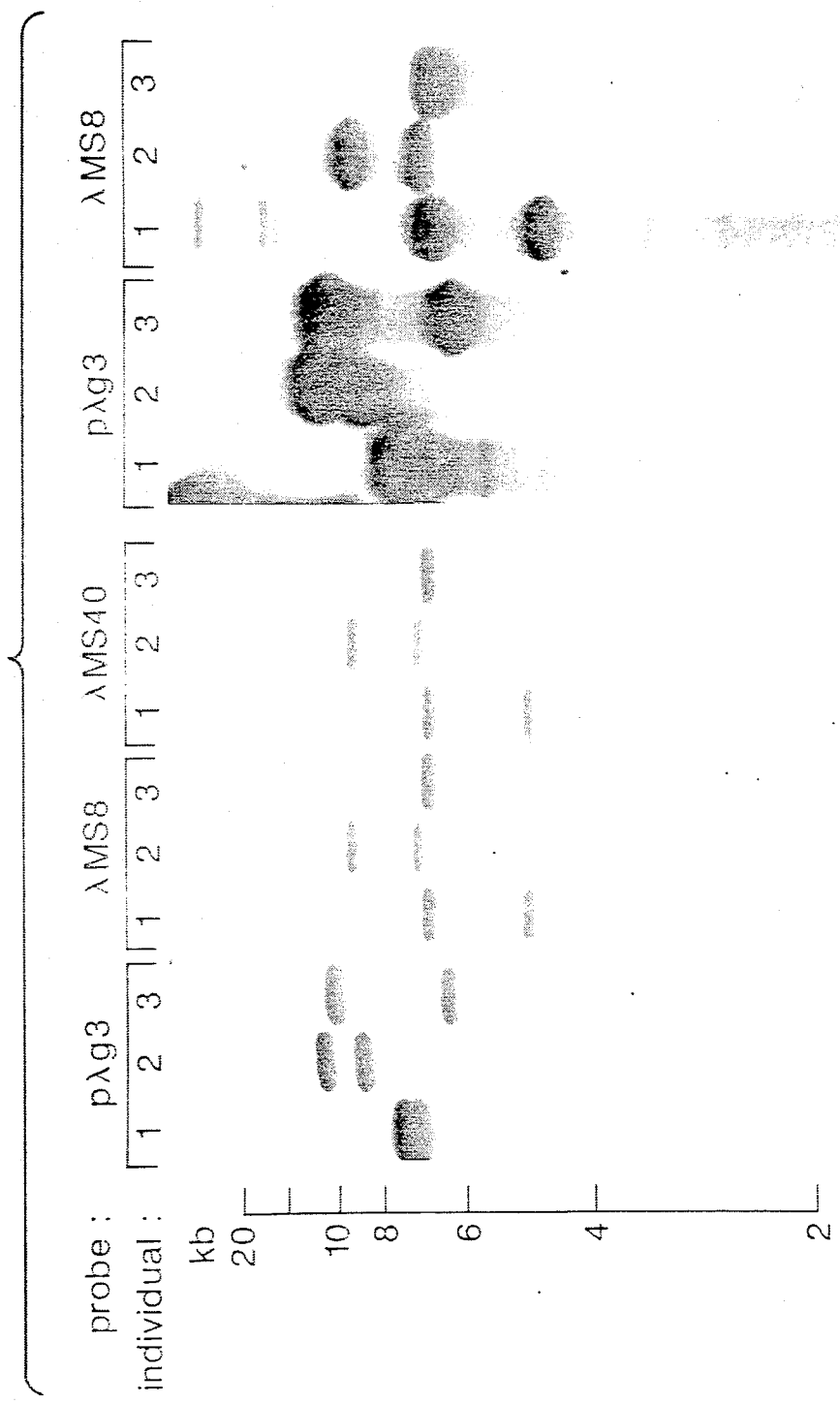
FIG. 5 shows the screening of λMS recombinants for locus specific hypervariable DNA probes.

FIG. 5 shows an Example of the screening of λMS recombinants for locus-specific hypervariable DNA probes. 2 μg samples of DNA from three unrelated individuals were digested with HinfI, eletrophoresed through a 0.8% agarose gel and Southern blot hybridized with $^{32}$p-labelled Sau3A inserts from pλg3 (Example 1),λMS40 as herein described in Materials and Methods. Filters were washed after hybridization in 0.1×SSC at 65°, and autoradiographed in the presence of an intensifier screen for 1 day (left panel) or 1 week (right panel). Note that λMS8 and λMS40 detect the same hypervariable locus, and that on prolonged autoradiography, additional variable DNA fragments are detectable.

The remaining recombinants λMS1, 31, 32 and 43 were derived from different loci which did not include the previously characterised pλg3 locus (see Example 1 and FIG. 5). Although none of these λMS recombinants produced DNA 'fingerprints' of multiple variable fragments, most λMS probes were seen to cross-hybridize weakly to additional polymorphic DNA fragments on prolonged autoradiographic exposure (FIG. 5).

Two of the λMS recombinants detected by probe 33.15, λMS3 and λMS30, failed to detect a specific locus in human DNA digested with HinfI or Sau3A, either in the presence or absence of human competitor DNA. On prolonged autoradiograph, both recombinants detected the same faint pattern of variable DNA fragments (data not shown). We have no explanation for this lack of locus-specificity, and these two MS recombinants have not been further characterized.

Thus despite previously reported difficulties in cloning large and unstable human minisatellites [see for example Nicholls et al (1985) Nucleic Acids Res. 13, 7569-7578 and Wyman et al (1985) Proc. Nath. Acad. Sci. USA 77, 6754-6758] we have been able to demonstrate that at least some of the largest and most variable DNA fragments detected in a DNA fingerprint are amenable to cloning in bacteriophage λ, provided that the inserts are stabilised by propagation of phage in a recBC *E. coli* host.

b) Determination of the repeat sequence units of cloned mini-satellites

Random segments of insert DNA from each λMS recombinant were sequenced to determine whether each cloned hypervariable locus consisted of tandem-repetitive minisatellite (see Materials and Methods). All λMS clones were shown to consist primarily of tandem repeat units ranging in length from 9 bp for λMS1 to 45 bp for λMS43 (FIG. 6).

FIG. 6 shows the consensus repeat sequence units of the λMS series of minisatellites. Random segments of each cloned minisatellite were sequenced to define the consensus repeat unit. Variable positions in each consensus are shown as: R, r=A or G; Y, y=C or T; N, n=any base. The minisatellite in MS8 consists of two mutually-interspersed repeat units 29 and 30 bp long. The consensus repeat sequence of pλg3 is also shown in FIG. 2. Each repeat sequence is aligned with the core sequence, with matches shown in uppercase, and a new core sequence derived from a comparison of the core with pλg3, λMS31 and λMS32 is also disclosed.

In no minisatellite are the repeat units completely homogeneous, consistent with the variation between repeat units seen at previously sequenced minisatellites (see British Patent Publication No. 2,166,445 and Example 1 herein. Most notably, the minisatellite in λMS8 consists of an intermingled array of two closely-related but distinct repeat units 29 and 30 bp long (FIG. 6). The end-points of the minisatellites in the λMS recombinants have not yet been determined.

Thus five new hypervariable loci have been isolated, each consisting mainly of a tandem-repetitive minisatellite. The tandem-repeat units of pλg3, λMS1, λMS31 and λMS32 each contain the core sequence, as expected (FIG. 6). However, the copies of the core sequence are imperfect, and comparisons of the repeat units of these minisatellites do not clearly define a new core sequence preferentially associated with these large and extremely variable loci. It seems likely instead that a wide range of core derivatives may be associated with large minisatellites. More notably, minisatellites λMS8 and λMS43 detected by probe 33.6, which consists of tandem repeats of a diverged version of the core sequence (see British Patent Publication No. 2,166,445), contain highly diverged versions of the core sequence (FIG. 2). Again, comparisons of λMS8, λMS43 and 33.6 do not clearly reveal a new specific sequence preferentially associated with these three loci (data not shown). It is clear that a detailed search for further sequence motifs associated with the most variable minisatellites, particularly those detected by probe 33.6, will require the analysis of a much larger spectrum of cloned minisatellites.

c) Mendelian inheritance and variability of loci detected by clones minisatellites The five new minisatellites isolated, λMS1, 8, 31, 32 and 43, each detect a single large and variable locus. Mendelian inheritance of all loci has been confirmed by analysing segregation in large horizontal pedigrees provided by the CEPH programme (FIG. 7).

Figure 7:
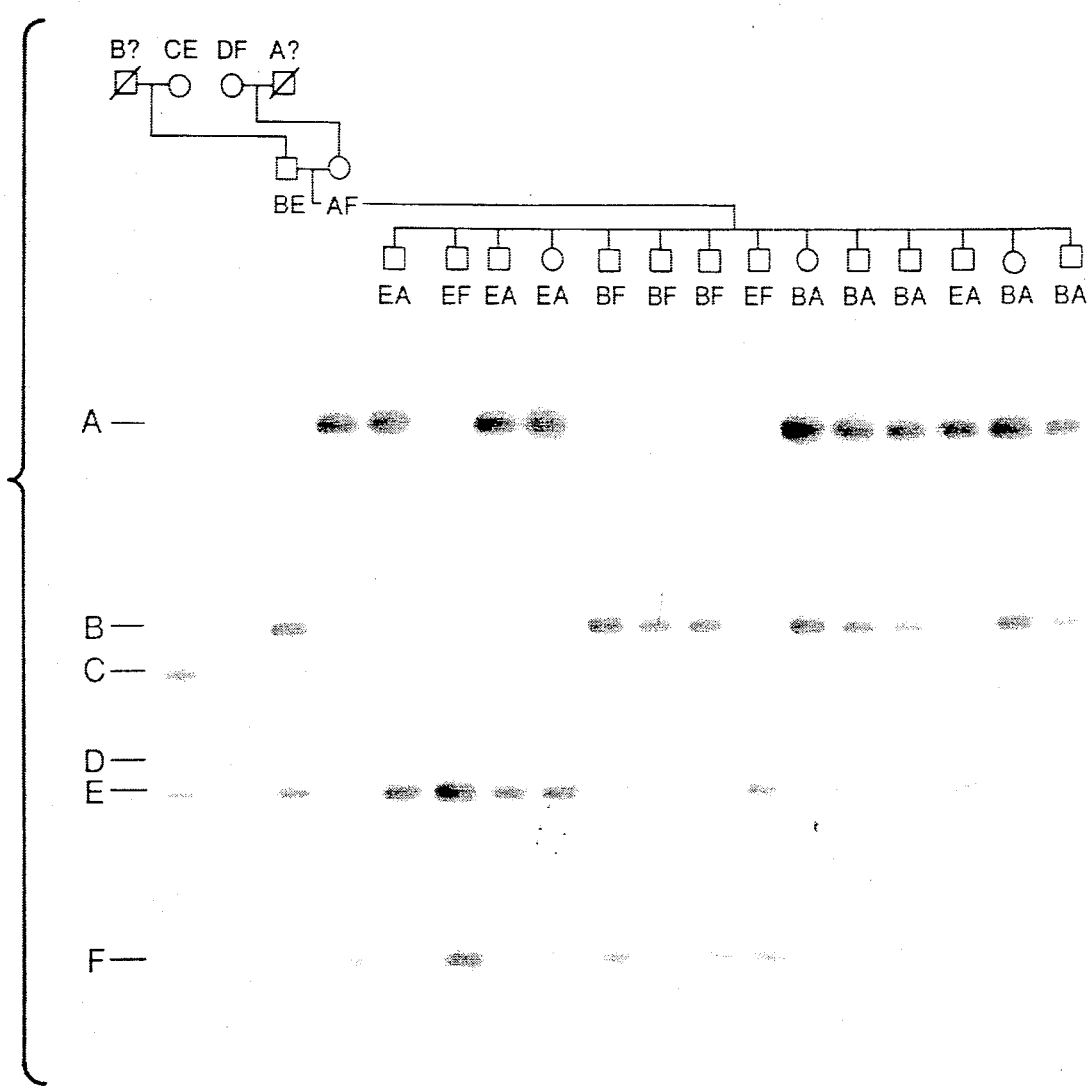
FIG. 7 shows the Mendelian inheritance of the hypervariable locus detected by the probe designated herein as λMS32.

FIG. 7 shows the Mendelian inheritance of the hypervariable locus detected by λMS32. 1 μg DNA samples from CEPH family 1413 were digested with Alu I and Southern blot hybridised to the $^{32}$P-labelled Sau 3A insert from λMS31. This family is completely informative at this locus.

Figure 8:
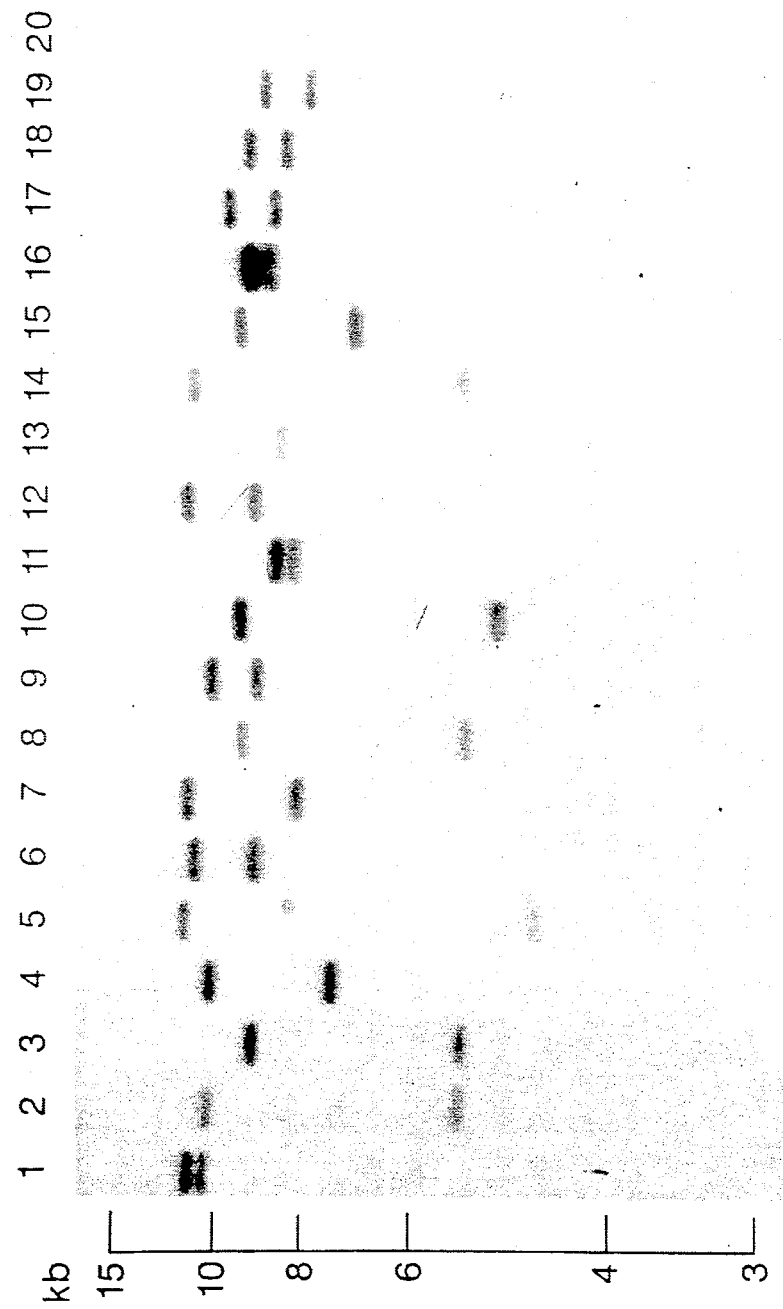
FIG. 8 shows an estimation of the allelic variability at the hypervariable locus detected by the probe designated herein as λMS43.

The extent of allelic variability for each probe has been estimated by analyzing the frequency of allele sharing between randomly-selected English individuals (FIG. 8). FIG. 8 provides an estimation of allelic variability at the hypervariable locus detected by MS43. 1 μg samples of DNA from twenty random-selected English people were digested with HinfI and Southern blot hybridized to λMS43. All individuals are heterozygous, indicating that the level of heterozygosity at this hypervariable locus is high ($H > 0.86$, $p > 0.95$). A more accurate estimate of heterozygosity may be made by comparing alleles in each individual with alleles in the six nearest neighbors on the autoradiograph to estimate the levels of allele sharing between individuals. For example, the larger allele in individual 5 appears to be present in 7, but not in 2, 3, 4, 6 and 8. Similarly, the smaller allele in 5 is not present in 2-4 or 6-8. Over all individuals examined, $s=0.11$, from which the mean allele frequence q can be estimated as $q = 1-(1-s)^{\frac{1}{2}} = 0.056$ and the heterozygosity as $(1-q) = 94\%$. This is a minimum estimate of heterozygosity limited by gel electrophoretic resolution.

Figure 9:
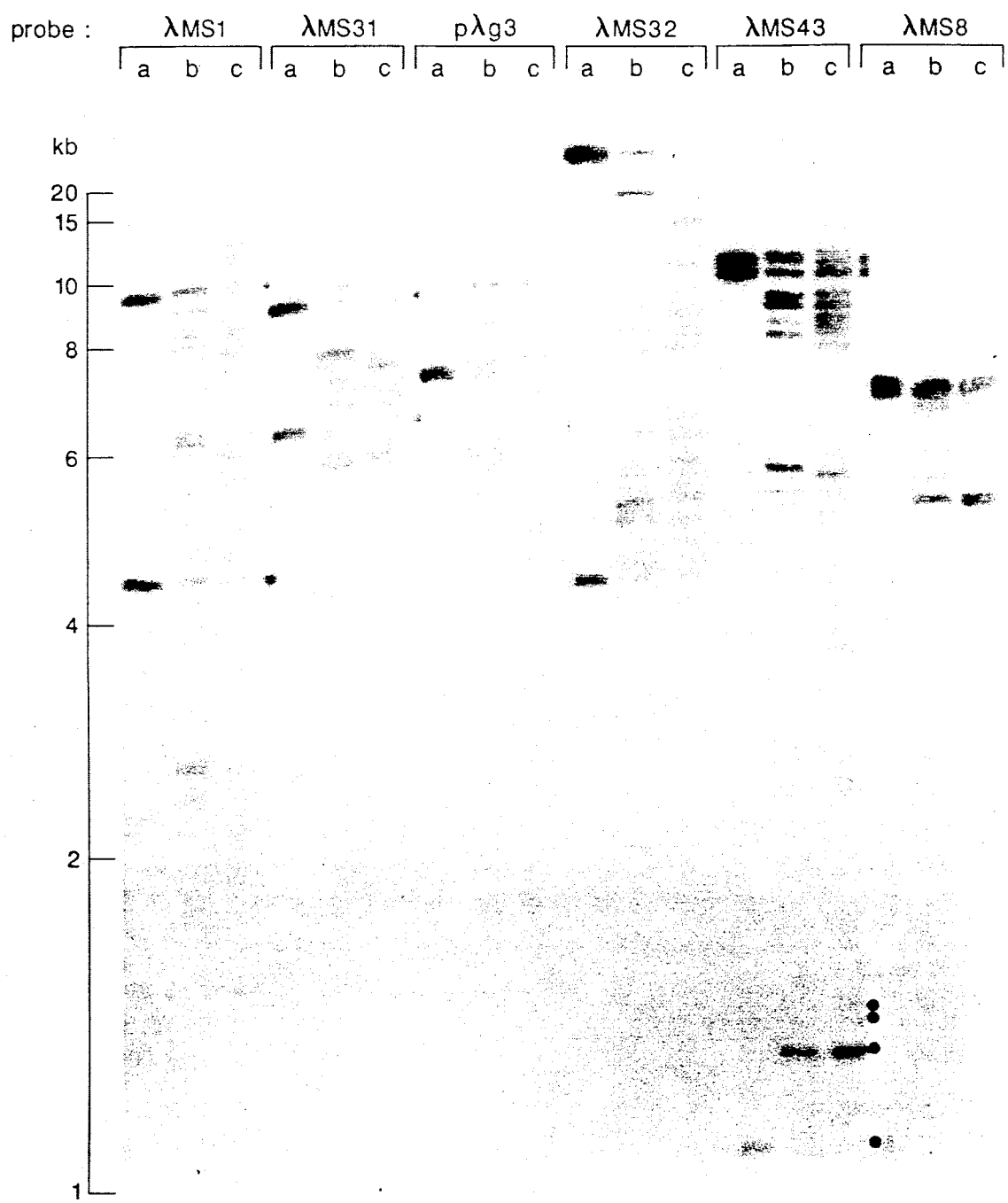
FIG. 9 shows an analysis of allelic length variation at hypervariable loci in pools of human DNA.

All loci are highly variable with heterozygosities ranging from 90% for λMS8 to 99% for λMS31 (see Table 1 above). The extent of allelic length variation has been further analysed by comparing the spectrum of alleles resolved in pools of 15 and 150 individuals (FIG. 9). FIG. 9 shows an analysis of allelic length variation at hypervariable loci in pools of human DNA. 10 μg samples of DNA from a single individual (a), from a pool of 15 individuals (b) and from a pool of 150 people (c) were digested with AluI (for λMS32) or HinfI (for all remaining probes) and Southern blot hybridized with the indicated locus-specific hypervariable probes. All individuals were randomly-selected North Europeans. Individual a was included within pool b, and all pool b individuals were included in pool c. It should be noted that λMS43 detects a second variable region represented by the short HinfI alleles marked 0; this region has not been further characterized.

For the least variable locus, λMS8, there are two predominant alleles 5.3 and 7.2 kb long plus 7 lower frequency alleles resolvable in the pool of 15 people. That the two predominant alleles are not the result of sampling error in these 15 individuals is shown by their similar prevalence in the pool of 150 individuals, together with a larger spectrum of low frequency alleles. Similarly, λMS43 (94% heterozygosity) shows 7 major alleles shared by the 15- and 150-individual pools, together with many minor alleles. In contrast, the most variable lociλMS1, 31 and 32 and pλg3, with heterozygosities estimated at 97–99%, show no alleles with a significant population frequency which are shared at equal intensity by both pools of individuals (with the exception of the shortest 1.6 kb allele of pλg3 as described hereinbefore, and thus the number of alleles at these loci is likely to be very high. For example, at least 50 different λMS32 alleles can be resolved in the pool of 150 individuals; this will be a minimal estimate of the total number of alleles limited by gel electrophoretic resolution.

The length dispersal of alleles in Caucasians also varies between these hypervariable loci (see FIG. 9 and Table 1). Most alleles of λMS31 are distributed fairly uniformly over a relatively narrow size range of 5.5–9.3 kb, whereas alleles of λMS1 vary in size from 2–20 kb. There is evidence in some cases of non-uniformity of allele length distribution; in particular λMS43 shows two predominant allelic size classes of 5–6 kb and 8–14 kb, and pλg3 shows three size classes of 1.6–1.7, 2.8–3.6 and 5–15 kb as hereinbefore described in Example 1.

As indicated above the loci detected are extremely variable and indeed are amongst the most polymorphic loci so far isolated from human DNA.

d) Chromosome assignment of hypervariable loci

None of the hypervariable locus-specific probes hybridize to rodent DNA, and therefore the segregation of these loci could be followed in man-rodent somatic cell hybrids [see FIG. 10 and Table 2 below]. The six loci were assigned to four different autosomes, with chromosomes 1 and 7 each bearing two hypervariable loci.

Figure 10:
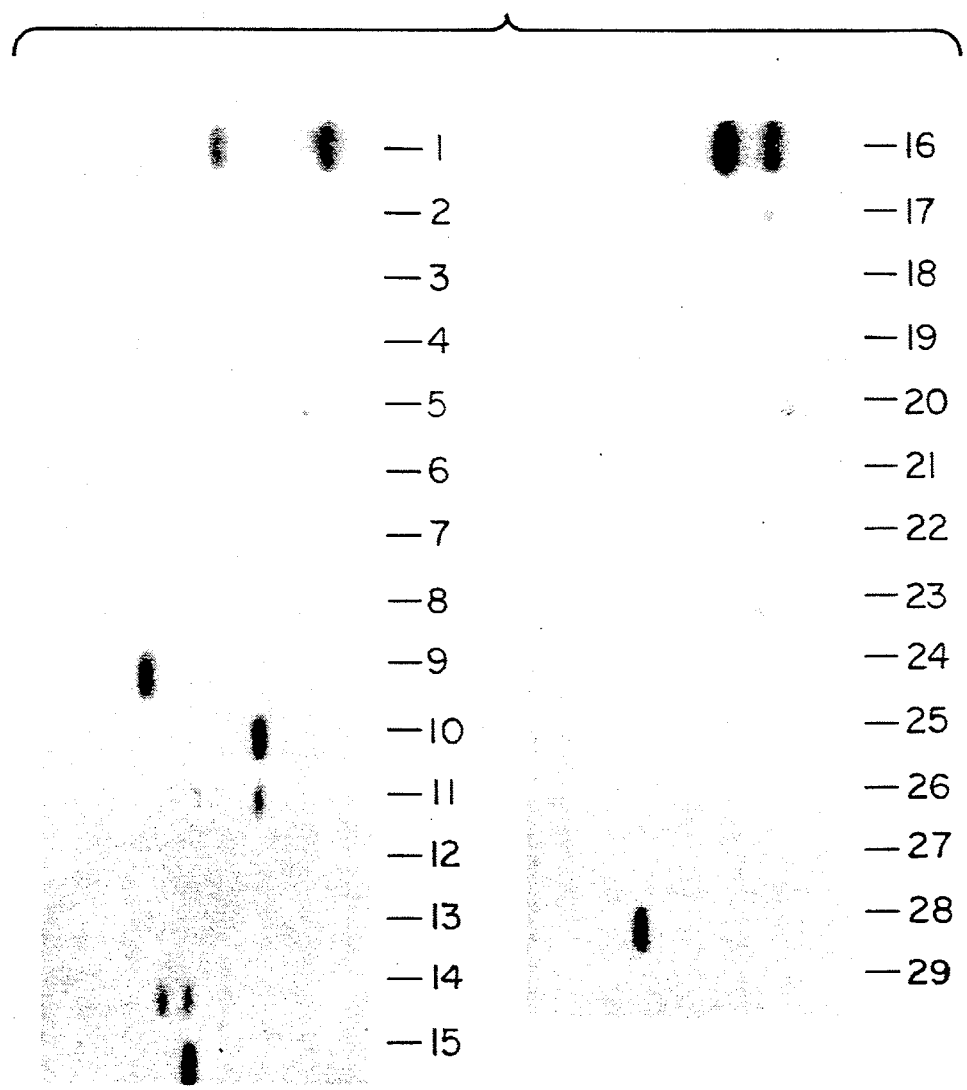
FIG. 10 shows the segregation of the hypervariable locus detected by the probe designated herein as λMS32, in a panel of human-rodent somatic cell hybrid DNAs digested with Alu I.

FIG. 10 shows the segregation of the hypervariable locus detected by λMS32 in a panel of human-rodent somatic cell hybrid DNAs digested with AluI. This locus cosegregates with human chromosome 1 (see Table 2 below). Interestingly, the hybrid cell line MOG 2C2 carried two alleles of both λMS32 and λMS1 (data not shown). This strongly suggests that both parental copies of human chromosome 1 have been retained in this hybrid, and, since all other positive hybrids contained only a single allele at each of these loci, this provides strong supporting evidence for synteny of λMS1 and λMS32. Hybrid F4SC13c112 contains chromosome 1p but is negative for λMS32; thus λMS32 is provisionally localized to chromosome 1q.

The following code is used in FIG. 10:

1. human 2
2. hamster
3. mouse
4. FG10
5. PCT BA18
6. 1α9498
7. SIF4A24EI
8. SIF15P5
9. CTP34B4
10. TWIN 19 D12
11. TWIN 19 F9
12. TWIN 19 F6
13. TWIN 19 C5
14. MOG 2C2
15. MOG 2E5
16. human 1
17. rat
18. DUR 4.3
19. FIR 5
20. C4A
21. DUR 4R3
22. 3W4 cl 5
23. clone 21
24. WILF 1
25. F4SC13 cl
26. SIF4A31
27. FST 9/10
28. HORL 411B6
29. HORP 9.5

Table 2 shows the chromosome assignment of hypervariable loci in human-rodent somatic cell hybrids.

TABLE 2

Chromosome assignment of hypervariable loci in human-rodent somatic cell hybrids

| chr. | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| 1  | − | − | − | − | − | − | − | P | − | − | + | − | − | − | − | − | − | + | + | + | − | − | + | + |
| 2  | − | − | − | − | − | − | − | − | − | − | − | − | + | − | − | − | + | + | − | P | + | − | − | − |
| 3  | + | − | − | + | − | − | − | − | + | + | + | − | − | − | − | − | − | + | + | + | + | + | + | + |
| 4  | − | − | − | − | − | − | − | − | + | + | − | − | − | − | − | + | − | − | + | − | + | + | + | + |
| 5  | − | M | − | + | − | − | − | − | M | − | − | − | + | − | − | − | − | M | − | − | − | − | − | + |
| 6  | − | − | − | − | − | − | − | − | + | + | − | − | − | − | + | − | + | + | + | + | + | − | − | + |
| 7  | − | D | − | − | + | + | − | − | − | − | − | − | − | − | − | − | − | + | + | N N | N N | + | + |
| 8  | − | − | + | N | − | − | − | − | − | − | + | − | − | + | − | − | − | − | + | + | + | + | + | + |
| 9  | − | − | − | − | − | − | − | − | + | N N | − | − | − | − | − | − | − | − | − | − | − | + | − | + |
| 10 | M | − | − | − | − | − | − | − | − | + | − | + | + | − | − | − | + | − | − | − | − | − | + | + |
| 11 | + | − | − | + | + | − | − | − | − | − | + | + | − | − | − | − | − | − | − | − | − | − | + | − |
| 12 | + | − | − | + | + | − | − | − | − | − | − | + | − | − | + | − | − | + | + | + | + | + | − | + |
| 13 | + | − | − | + | − | − | − | − | − | + | + | − | − | − | − | − | − | − | N N | N N | − | + |
| 14 | + | M | − | + | + | − | − | + | + | + | − | + | − | − | − | − | + | + | + | + | + | + | + | + |
| 15 | + | − | − | − | + | − | − | − | − | + | + | − | + | − | − | − | + | − | − | − | − | − | + | + |
| 16 | − | − | − | − | − | − | − | − | − | + | − | − | − | − | − | − | − | + | + | − | − | − | + | + |
| 17 | + | − | − | + | + | − | − | − | − | − | − | + | − | + | − | + | + | + | + | + | + | + | − | + |
| 18 | + | + | − | + | − | − | − | − | − | − | + | + | − | + | − | − | − | + | + | + | + | + | + | + |
| 19 | − | − | − | − | − | − | + | − | − | − | − | − | − | − | − | − | − | − | − | − | − | − | + | − |
| 20 | M | − | − | M | − | − | − | − | − | + | − | − | − | − | − | − | + | − | + | + | + | + | − | − |
| 21 | + | − | − | + | + | − | − | − | − | − | − | + | + | − | + | − | − | + | + | + | + | + | + | + |

TABLE 2-continued

Chromosome assignment of hypervariable loci in human-rodent somatic cell hybrids

| chr. | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | |
|---|---|---|---|---|---|---|---|---|---|---|---|---|---|---|---|---|---|---|---|---|---|---|---|---|---|
| 22 | + | − | M | + | − | − | − | − | M | − | N | − | − | − | − | − | − | − | − | − | + | + | − | N | N |
| X | + | + | − | − | + | − | − | + | + | + | + | + | − | + | + | + | + | − | − | − | − | − | + | + | |
| pλg3 | − | − | − | − | + | + | − | M | M | − | − | − | − | − | − | − | + | + | − | − | − | + | + | | chr. 7 17/17 |
| λMS1 | − | − | M | − | − | − | − | + | − | − | − | + | − | − | − | − | + | + | + | − | − | − | + | + | chr. 1 22/22 |
| λMS8 | − | N | − | + | − | − | − | − | − | − | − | + | − | − | − | − | + | − | − | − | − | + | − | chr. 5 20/21 |
| λMS31 | − | + | − | − | + | + | − | − | − | − | − | − | − | − | − | − | + | + | − | − | − | − | + | + | chr. 7 20/20 |
| λMS32 | − | − | − | − | − | − | − | − | − | + | − | − | − | − | − | − | + | + | − | − | − | + | + | chr. 1 23/23 |
| λMS43 | + | − | − | + | + | − | − | − | − | + | − | + | − | − | + | − | − | + | + | + | + | − | − | + | chr. 12 24/24 |

In Table 2 the following somatic cell hybrids were typed:
1, DUR4.3; 2, FIR5; 3, C4A; 4, DUR4R3; 5, 3W4c15; 6, clone 21; 7, WILF.1; 8, F4SC13c112; 9, SIF4A31; 10, FST9/10; 11, HORL411B6; 12, HORP9.5; 13, FG10; 14, PCTBA18; 15, 1α9498; 16, SIF4A24E1; 17, SIF15P5; 18, CTP34B4; 19TWIN 19D12; 20, TWIN 19F9; 21, TWIN 19F6; 22, TWIN 19C5; 23, MOG 2C2; 24, MOG 2E5 and the meaning of the symbols employed in the Table are as follows:

+, chromosome or hypervariable locus present; −, chromosome or locus absent; M, chromosome present in only some cells or locus only weakly detected by Southern blot hybridization; N, chromosome not tested or equivocal result, locus not tested; P, short arm present; D, chromosome 7pter→q22 present as a 7/X translocation. The deduced chromosome assignment of each locus-specific hypervariable probe is given, together with the fraction of unambiguously informative cell hybrids which are concordant for the presence or absence of the intact chromosome and the hypervariable locus. For each hypervariable probe, all chromosomes except one were multiply excluded by this analysis.

The hybridization of λMS1 to hybrid 8 (F4SC13c112) containing chromosome 1p suggests that λMS1 is located on 1p. Conversely, λMS32 does not hybridize to hybrid 8, suggesting localization to 1q. pλg3 does not hybridize to hybrid 2 (FIR5) which contains chromosome 7pter→q22. Furthermore, hybrids JDA 13.1 and JDA 3 containing 7pter→q31.3 and 7q31.3→qter respectively are negative and positive respectively for pλg3 (data not shown), localizing pλg3 to 7q31.3→qter. Conversely, λMS31 hybridizes to FIR5 and JDA 13.1 but not JDA 3, suggesting a localization to 7pter→q22. This lack of clustering was confirmed by linkage analysis in large CEPH sibships, which showed no significant linkage between either pair of syntenic markers (z > −2 at > 0.35 for each pair, data not shown).

All six cloned minisatellite loci, including pλg 3 described in Example 1, are autosomal and dispersed; of the two syntenic pairs of minisatellites found, neither show significant pair-wise linkage. This autosomal localization and lack of clustering is fully consistent with previous results from segregation analysis of DNA fingerprints which showed that the numerous hypervariable DNA fragments detected by polycore probes are derived from multiple and dispersed autosomal loci, although the chromosome localization of individual fragments could not be deduced from DNA fingerprints.

The cloned minisatellites so far localized tend to be derived from the larger human autosomes (Table 1), as expected if they are dispersed randomly over the human genome. In the absence of precise regional localization, it remains possible that these minisatellites are preferentially located at centromeres and telomeres, which are rich in simple sequence satellite DNA. However, segregation analysis of DNA fingerprint fragments in recombinant inbred strains of mice has shown that murine minisatellites are not preferentially associated with centromers or telomeres, and it is likely that their human counterparts are similarly dispersed.

EXAMPLE 3

Minisatellite probe sensitivity and forensic applications

The tandem repetitive minisatellite probes which have been tested are very sensitive, presumably as a result of the repetitive nature of both the hybridization probe and the target minisatellite DNA. The Southern blot autoradiographic signal obtained after overnight hybridization is saturated at probe DNA concentrations of >0.1 ng/ml (data not shown), and signals can be readily obtained from 60 ng or less of human genomic DNA (see FIG. 11A). Similarly, depending on the genotypes of the individuals tested, these probes can detect an admixture of 2% or less of one individual's DNA with another (see FIG. 11B).

The sensitivity and variability of these locus-specific minisatellite probes makes them particularly useful in forensic medicine. FIG. 11C shows an analysis of semen stains from two victims who had been sexually assaulted and murdered, where the recovery of DNA from the second victim was insufficient for conventional DNA fingerprint analysis which requires at least 0.5 μg DNA per test (see UK Patent Publication No. 2,166,445).

Figure 11B:

Thus FIG. 11 shows an assessment of the sensitivity of locus specific probes and their application to the forensic analysis of a double rape/murder case. In FIG. 11A decreasing amounts of human DNA digested with HinfI were Southern blot hybridized with $^{32}$P-labelled insert DNA from MS1. Filters were autoradiographed in the presence of an intensifier screen for 1 week. In FIG. 11B decreasing amounts of individual A DNA were mixed with 4 μg individual B DNA in the indicated ratios, and Southern blot hybridized, with λMS1 as in FIG. 11A. In FIG. 11C victims X and Y had been sexually assaulted and murdered. A suspect Z had been charged with the murder of Y, and forensic evidence further suggested that both X and Y had been murdered by the same individual. DNA from the following forensic specimens was isolated and analysed: a, hair from X taken two days post-mortem; b, a mixture of semen and vaginal fluid recovered from the pubic hair of X; c, fresh blood from suspect Z; d, cardiac blood taken one day post-mortem from Y; e, vaginal swab from Y bearing semen, blood and vaginal material; F, a stain from Y's skirt bearing semen and blood. Samples a and b had been stored dry at 4° for 3 years, samples d and e at 4° for 2 months and sample f stored dry at 4° for 2 months. DNA was extracted following the procedures of Gill, Jeffreys and Werrett (1985) Nature 318, 577–579, digested with HinfI and Southern blot hybridized to $^{32}$p-labelled λMS1 insert. 0.8 μg DNA was analyzed in each sample, except for sample e (0.1 μg DNA) and f (0.04 μg DNA). Autoradiography was for one week in the presence of an intensifier screen. Note that the semen stains b, e and f each contain two hybridizing DNA fragments which are not attributable to the victim. In addition, sample b contains the victim's alleles derived from vaginal DNA. The semen alleles in b, e and f are indistinguishable, suggesting that victims X and Y had indeed been sexually assaulted by the same man. The alleles of suspect Z do not match those of the semen stains.

These results were confirmed by hybridization with λMS31 (data not shown) and by DNA fingerprint analysis of larger amounts of forensic material. In the light of this evidence, the charges preferred against the suspect were discontinued by the crown prosecutor.

EXAMPLE 4

Pooled minisatellite probes

The sensitivity of these minisatellites in Southern blot hybridizations permits pools of probes to be used to detect variable DNA fragments from several loci simultaneously, as shown for a pool of 5 probes (pλg3, λMS1, λMS8, λMS31 and λMS43) in FIG. 10. In theory, the number of different DNA fragments detectable by 5 probes is $$\sum_{1}^{5} (1 + H_i).$$

where $H_i$ is the heterozygosity of the i th probe. For these 5 probes, on average 9.78 fragments should be detected per individual. In practice, 8.4±1.2 (S.D.) bands >2 kb are resolved (40 randomly selected individuals tested). This loss of resolvable bands is partly due to exclusion of the small (1.6 kb) and relatively common pλg3 allele (Example 1, mean loss per individual=0.33 band), but is mainly the result of electrophoretic comigration of different minisatellite alleles.

The multilocus Southern blot patterns are highly individual-specific with only 18% (S.D.±11%) of DNA fragments shared between pairs of randomly-selected North Europeans (40 pairs tested). For sibs, the level of fragment sharing rises as expected to −57% (10 sib pairs tested).

In father/mother/child trios, all offspring fragments can be traced back to the parents (FIG. 12). Each offspring contains 3.4±0.5 (S.D.) DNA fragments which are specifically of paternal origin, and an equal number of maternal-specific DNA fragments (10 father/mother/child trios tested).

Thus as indicated above, FIG. 12 shows the detection of multiple hypervariable loci in human DNA by hybridisation with pooled minisatellite probes. 4 μg DNA samples from a random selection of English people (1-6), from sib pairs (7, 8 and 9, 10) and from father/child/mother family groups (11, 12, 13 and 14, 15, 16) were digested with HinfI and electrophoresed through a 0.8% agarose gel until all fragments less than 2 kb had electrophoresed off the gel. The digests were Southern blot hybridized with 2 ng of insert DNA from each pλg3, λMS1, λMS8, λMS31 and λMS43; inserts were pooled prior to labelling with $^{32}$p by random oligonucleotide priming. Variations in band labelling intensity presumably arise from variability in the efficiency of labelling and hybridization of individual probes.

I claim:

1. A method of characterizing a test sample of genomic DNA from a donor by reference to one or more controls which method comprises:
   i) fragmenting said sample DNA with at least one restriction enzyme which does not cleave a sequence corresponding to a tandem repeat,
   ii) probing the DNA fragments with a polynucleotide probe which specifically hybridizes to a single minisatellite region (to the exclusion of other regions),
   wherein said probe consists essentially of up to 10,000 tandem repeats of a repeat sequence unit being one of

| | |
|---|---|
| AGGAATAGAAAGGCGGGYGGTGTGGGCAGGGAGRGGC | 3 |
| GTGGAYAGG | 4 |
| TGGGAGGTGGRYAGTGTCTG | 5 |
| GAATGGAGCAGGYGRCCAGGGGTGACTCA | 6 |
| GGGCTGGGGAGATGGTGGAGGAGGTGTTGG | 7 |
| AGGCTGGGGAGATGGTGGAGGAAGAGTAC | 8 | and

| | |
|---|---|
| TGTGTGTAATGGGTATAGGGAGGGCCCCGGGA | 9 |
| AGGGGGTGTGGYX | | wherein Y is C, T or U, X is G or C, R is A or G and T is T or U, or a sequence complementary thereto of identical length,
   iii) detecting hybridized fragments of DNA, and
   iv) comparing the hybridized fragments with the said control or controls.

2. The method according to claim 1 wherein said method establishes the identity of the test sample donor with one or more control sample donors, wherein the control sample(s) are fragmented in an identical manner and a comparison is made of the hybridized fragments from the control and test samples.

3. The method according to claim 1 wherein said method establishes a family connection between the test sample donor and one or more control sample donors, wherein the control sample(s) are fragmented in an identical manner and a comparison is made of the hybridized fragments from the control and test samples.

4. The method as claimed in claim 1 wherein said probing is effected using at least two of said polynucleotide probes either in a sequence of tests or in a single test using a mixture of said polynucleotide probes.

5. The method as claimed in claim 1 wherein the repeat unit sequence of the polynucleotide probe consists of one of sequences 3-9.

6. The method as claimed in claim 1 wherein the polynucleotide probe is from 9 bp to 45 bp.

7. The method as claimed in claim 1 wherein the polynucleotide probe is wholly in single stranded form.

8. A method as claimed in claim 1 wherein the polynucleotide probe is selected from the group consisting of pλg3, λMS1, λMS8(1), λMS8(2), λMS31, λMS32 and λMS43.

* * * * *